(12) United States Patent
Nishiura et al.

(10) Patent No.: US 10,098,434 B2
(45) Date of Patent: Oct. 16, 2018

(54) SPRAYER

(71) Applicants: SUNSTAR INC., Takatsuki-shi, Osaka (JP); Maxell Holdings, Ltd., Otokuni-gun, Kyoto (JP)

(72) Inventors: Masahiro Nishiura, Takatsuki (JP); Akio Yonetani, Takatsuki (JP); Hironobu Nagano, Ibaraki (JP); Kazuhiko Inoue, Ibaraki (JP); Yugo Watari, Ibaraki (JP); Yusuke Okamoto, Ibaraki (JP)

(73) Assignees: Sunstar Inc., Takatsuki-shi (JP); Maxell Holdings, Ltd., Kyoto (JP)

( * ) Notice: Subject to any disclaimer, the term of this patent is extended or adjusted under 35 U.S.C. 154(b) by 148 days.

(21) Appl. No.: 14/916,932

(22) PCT Filed: Sep. 4, 2014

(86) PCT No.: PCT/JP2014/073336
§ 371 (c)(1),
(2) Date: Mar. 4, 2016

(87) PCT Pub. No.: WO2015/034002
PCT Pub. Date: Mar. 12, 2015

(65) Prior Publication Data
US 2016/0192760 A1    Jul. 7, 2016

(30) Foreign Application Priority Data

Sep. 9, 2013  (JP) ................................ 2013-186157
Sep. 9, 2013  (JP) ................................ 2013-186158

(51) Int. Cl.
*A45D 34/04* (2006.01)
*A61M 11/06* (2006.01)
(Continued)

(52) U.S. Cl.
CPC ............. *A45D 34/04* (2013.01); *A45D 19/02* (2013.01); *A61M 11/06* (2013.01); *A61M 15/02* (2013.01);
(Continued)

(58) Field of Classification Search
CPC ... B05B 7/0483; B05B 7/2405; B05B 7/2408; B05B 7/2416; B05B 7/2424;
(Continued)

(56) References Cited

U.S. PATENT DOCUMENTS 5,192,009 A * 3/1993 Hildebrandt .......... B05B 7/0433
222/400.5
6,997,396 B2 * 2/2006 Fedorov ................ B05B 7/2416
239/311
(Continued)

FOREIGN PATENT DOCUMENTS

EP    0 339 109 A1 *  4/1988  .......... B05B 7/2416
JP    S58-44029 B2     9/1983
(Continued)

OTHER PUBLICATIONS

International Search Report of PCT/JP2014/073336.
Written Opinion of PCT/JP2014/073336 dated Dec. 2, 2014.

*Primary Examiner* — Steven J Ganey
*Assistant Examiner* — Cody Lieuwen
(74) *Attorney, Agent, or Firm* — Crowell & Moring LLP

(57) ABSTRACT

Provided is a sprayer usable as a cosmetic mist device and an inhaler. The sprayer includes an air pump, a motor, a battery, a mist nozzle, a tank for storing a mist liquid concentrate, and a vertically long, cylindrical, main body case. The main body case is divided into front and back chambers by a division wall, and the tank is housed in the front chamber. The air pump, the motor, and an electrical component section including the battery are disposed, in this
(Continued)

Figure 1:
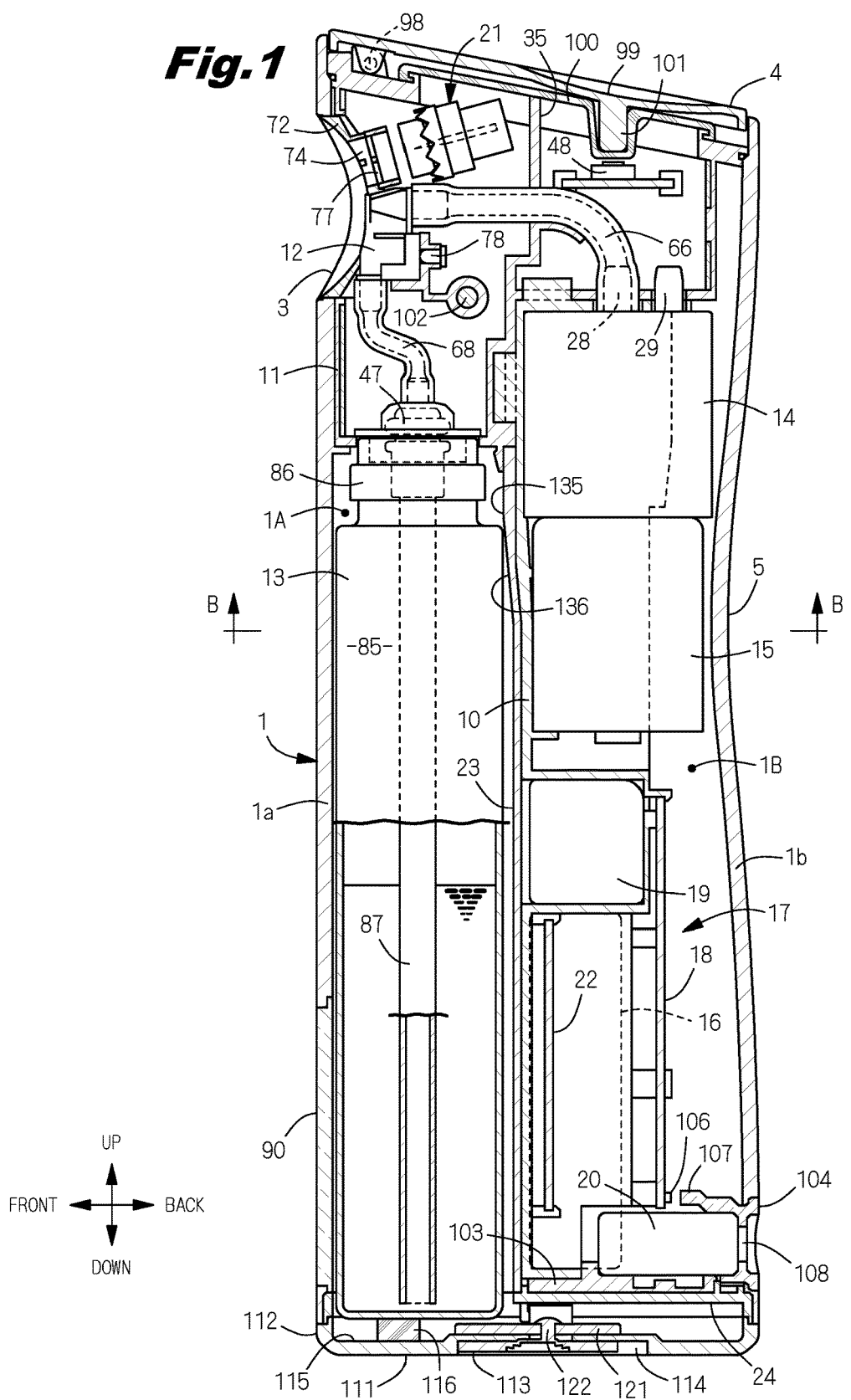

order, in the back chamber. The tank is formed in a vertically long shape occupying most of the front chamber without affecting an outer shape of the main body case. A grip portion is formed in a recessed manner at an upper portion of a back face of the main body case and the air pump and the motor are disposed near the grip portion.

14 Claims, 12 Drawing Sheets

(51) Int. Cl.
| | |
|---|---|
| *A61M 15/02* | (2006.01) |
| *A45D 19/02* | (2006.01) |
| *B05B 7/24* | (2006.01) |
| *B05B 15/65* | (2018.01) |
| *A61H 33/12* | (2006.01) |
| *B05B 5/16* | (2006.01) |

(52) U.S. Cl.
CPC .......... *B05B 7/2416* (2013.01); *B05B 7/2424* (2013.01); *A45D 2200/057* (2013.01); *A45D 2200/202* (2013.01); *A45D 2200/205* (2013.01); *A61H 33/12* (2013.01); *A61H 2201/0153* (2013.01); *A61H 2201/5043* (2013.01); *A61M 2205/07* (2013.01); *A61M 2205/8206* (2013.01); *B05B 5/1691* (2013.01); *B05B 15/65* (2018.02)

(58) Field of Classification Search
CPC ....... B05B 7/2489; B05B 7/2491; B05B 5/03; B05B 5/1691; B05B 9/0855; B05B 9/861; B05B 15/65; A45D 19/02; A45D 34/04; A45D 2200/057; A45D 2200/202; A45D 2200/205; A61M 11/02; A61M 11/06; A61M 15/02; A61M 2205/07; A61M 2205/8206; A61H 2201/0153; A61H 2201/5043
USPC ....... 239/153, 154, 318, 337, 340, 344, 346, 239/351, 375, 426, 434, 120, 121, 600, 239/332; 222/173, 182, 204, 333, 630, 222/635, 637
See application file for complete search history.

(56) References Cited

U.S. PATENT DOCUMENTS

| | | | | |
|---|---|---|---|---|
| 7,178,743 | B2* | 2/2007 | Clarke, III | ............ B05B 7/2416 239/304 |
| 8,319,654 | B2* | 11/2012 | Field | ............ A47L 13/26 204/194 |
| 8,757,516 | B2* | 6/2014 | Spiegel | ............ B05B 7/068 239/423 |

FOREIGN PATENT DOCUMENTS

| | | |
|---|---|---|
| JP | 1986-109545 U | 7/1986 |
| JP | S62-09872 Y2 | 3/1987 |
| JP | 2012-065895 A | 4/2012 |
| JP | 2014-000517 A | 1/2014 |

* cited by examiner

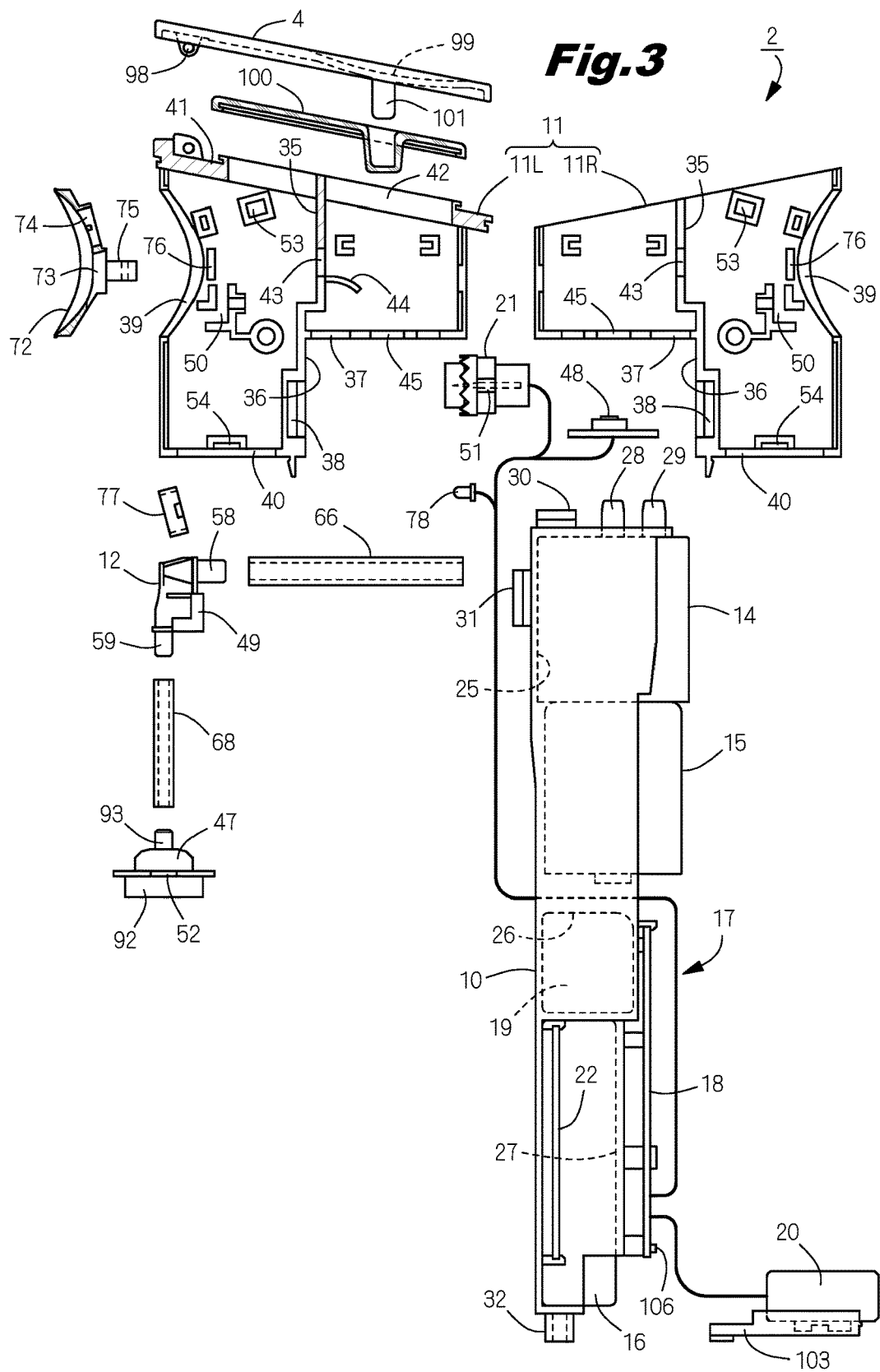

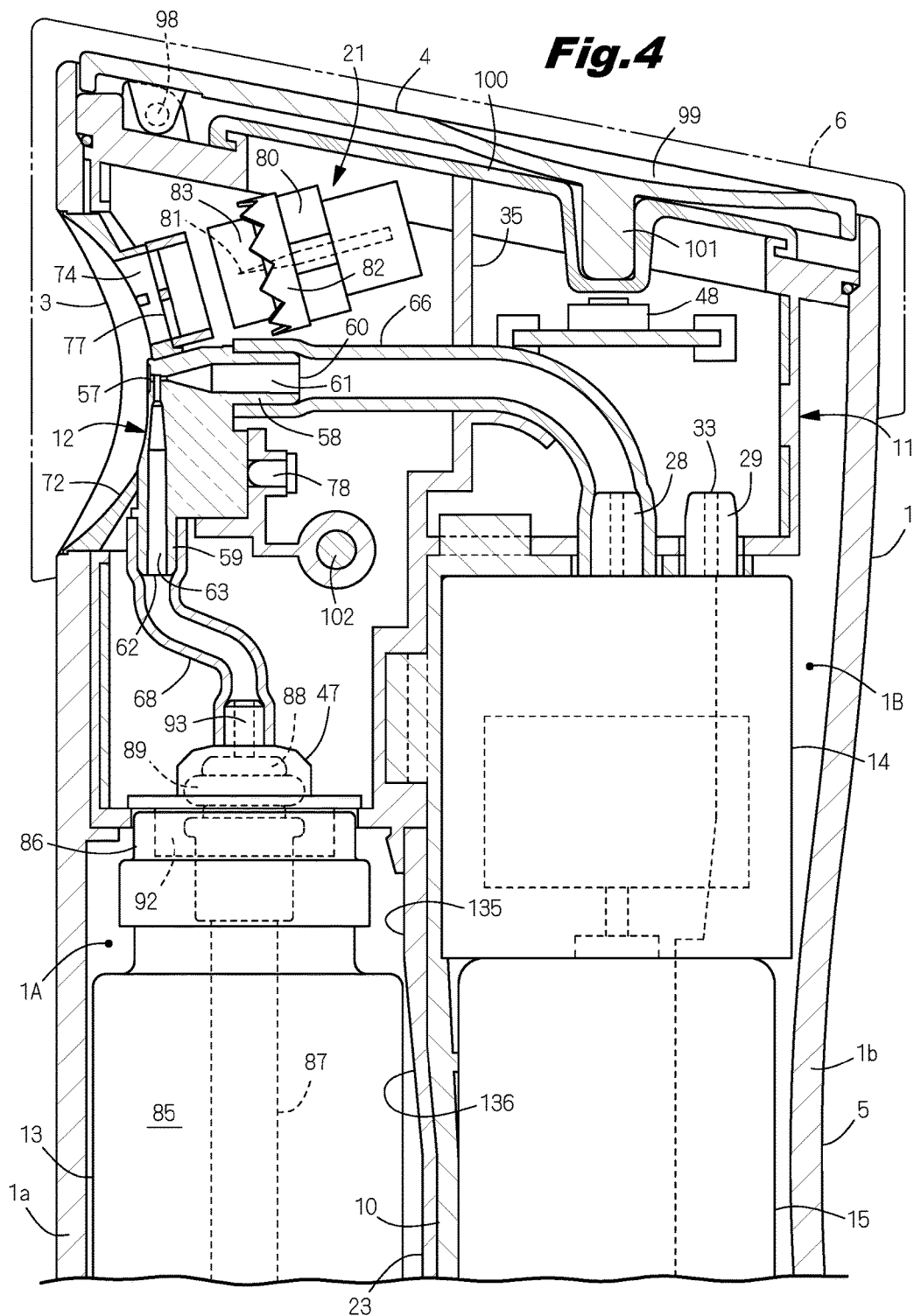

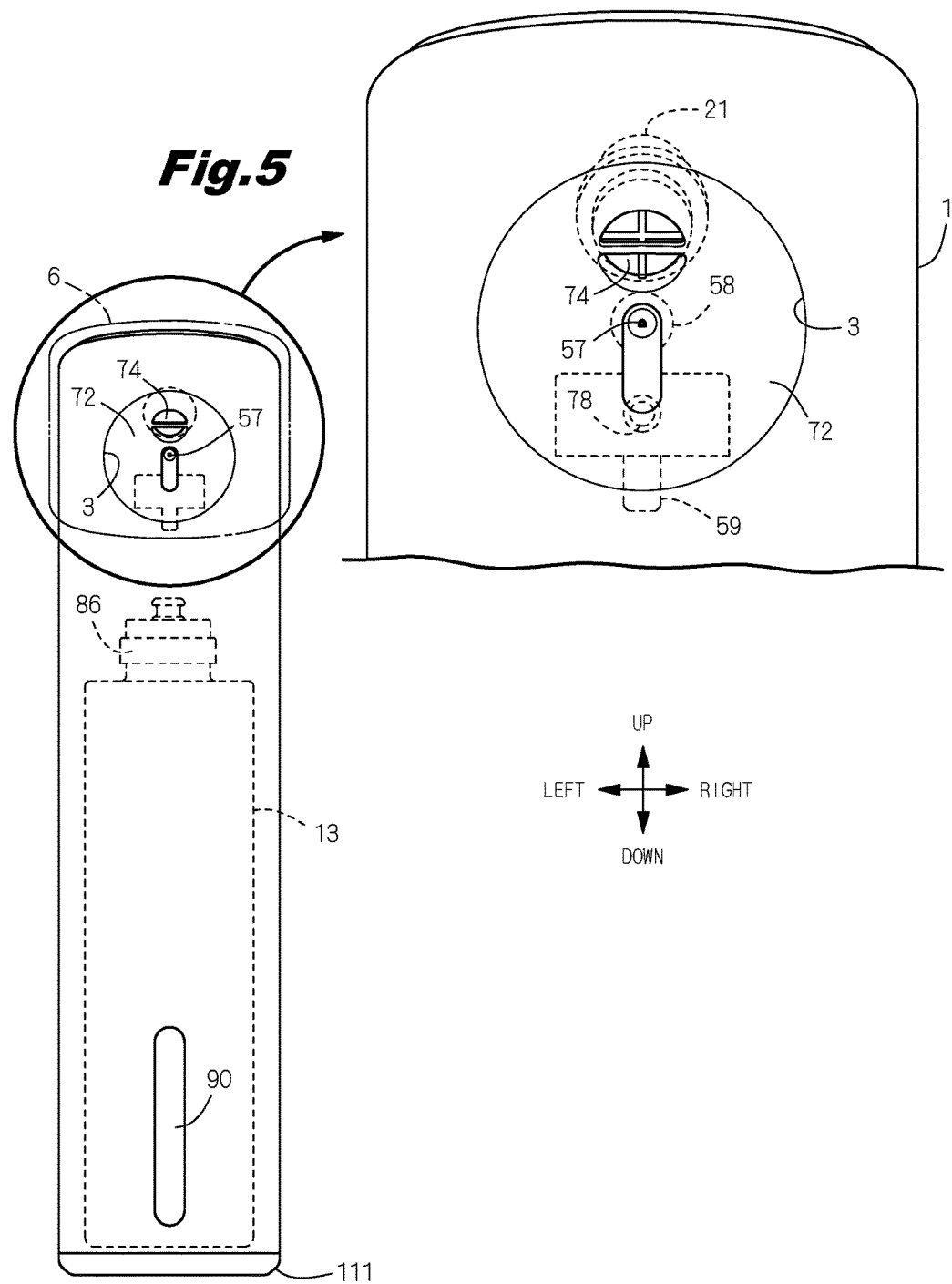

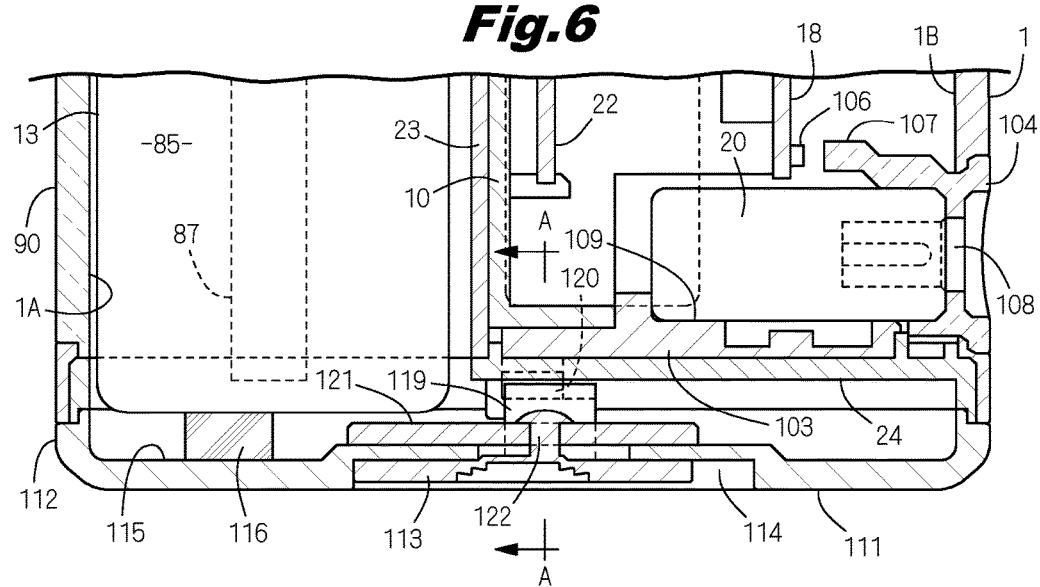
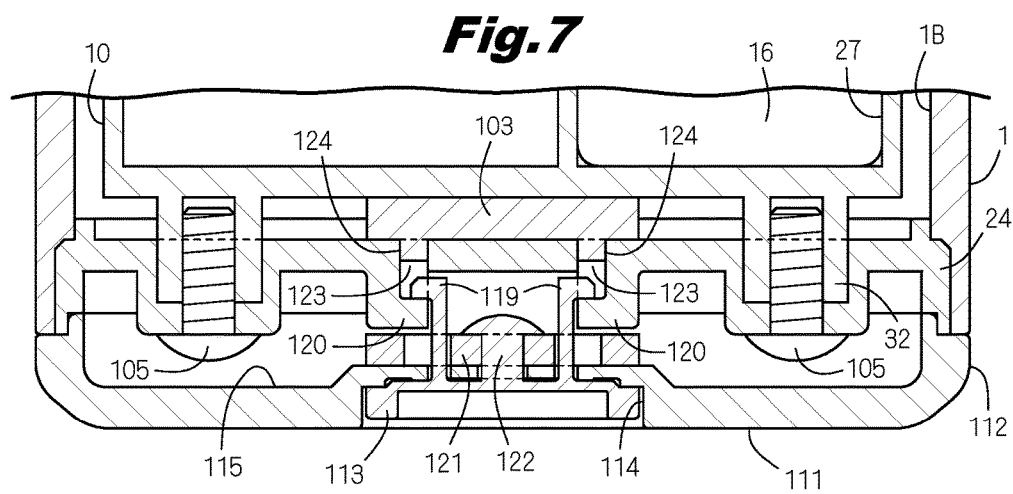

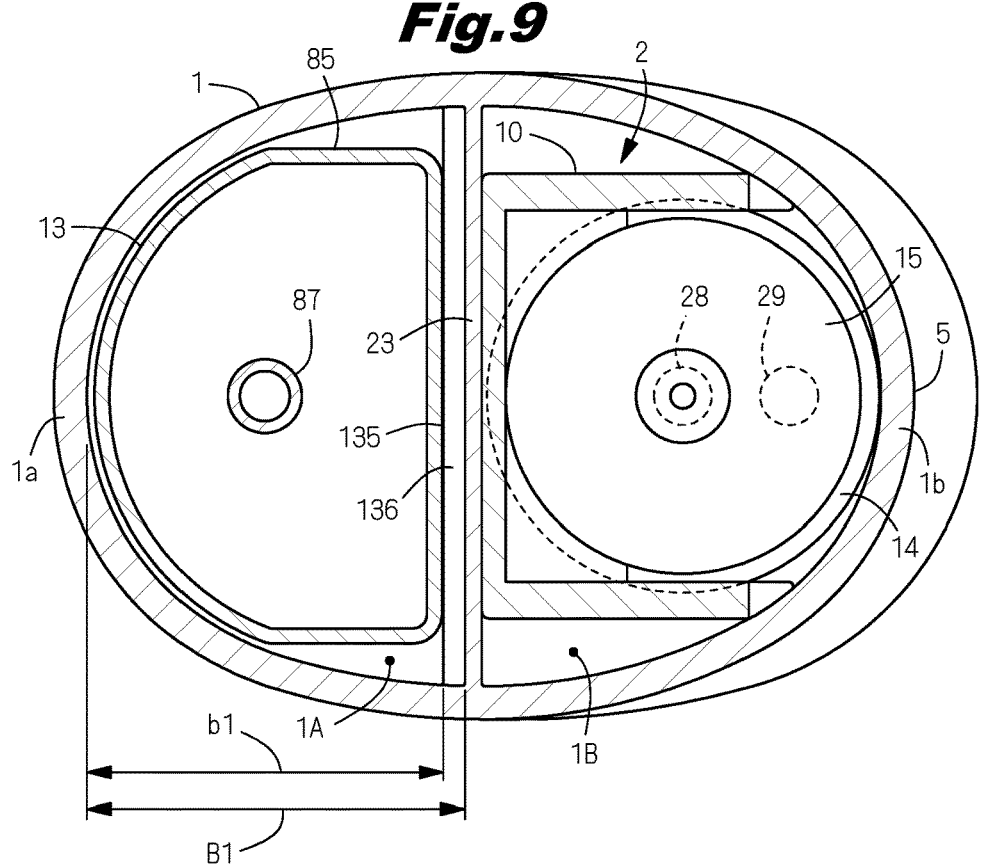
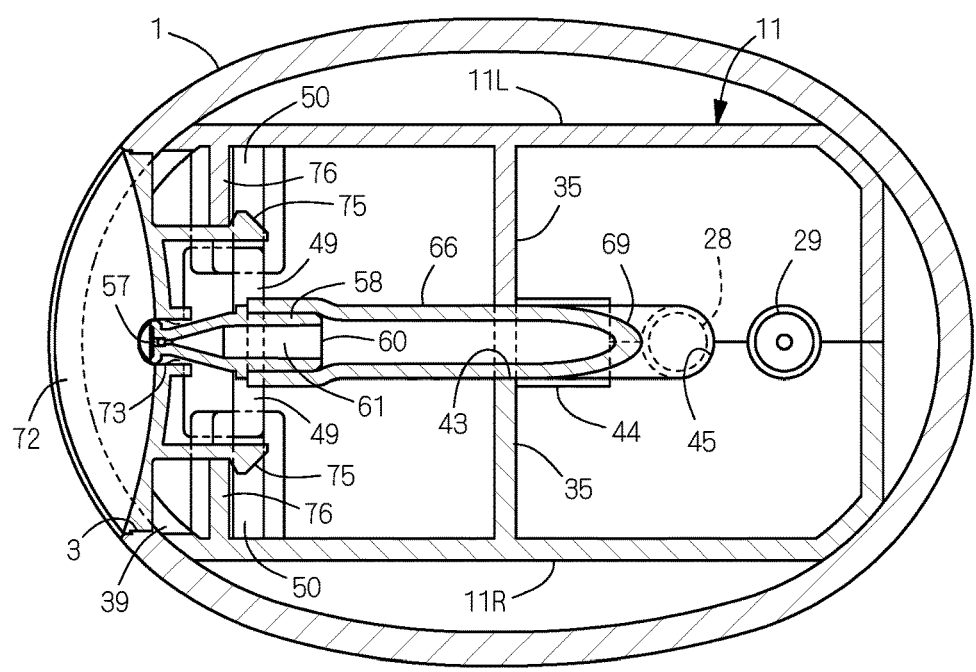

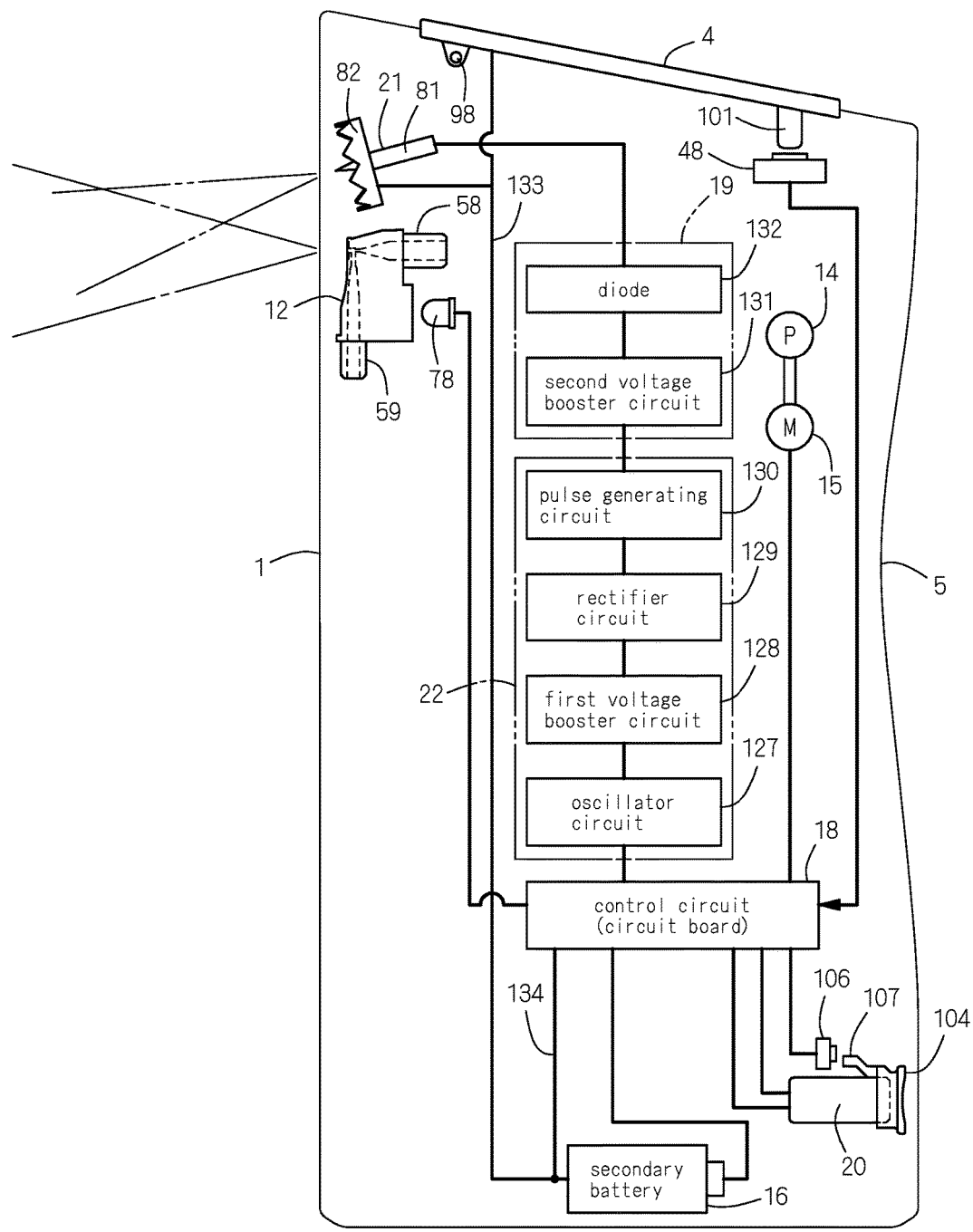

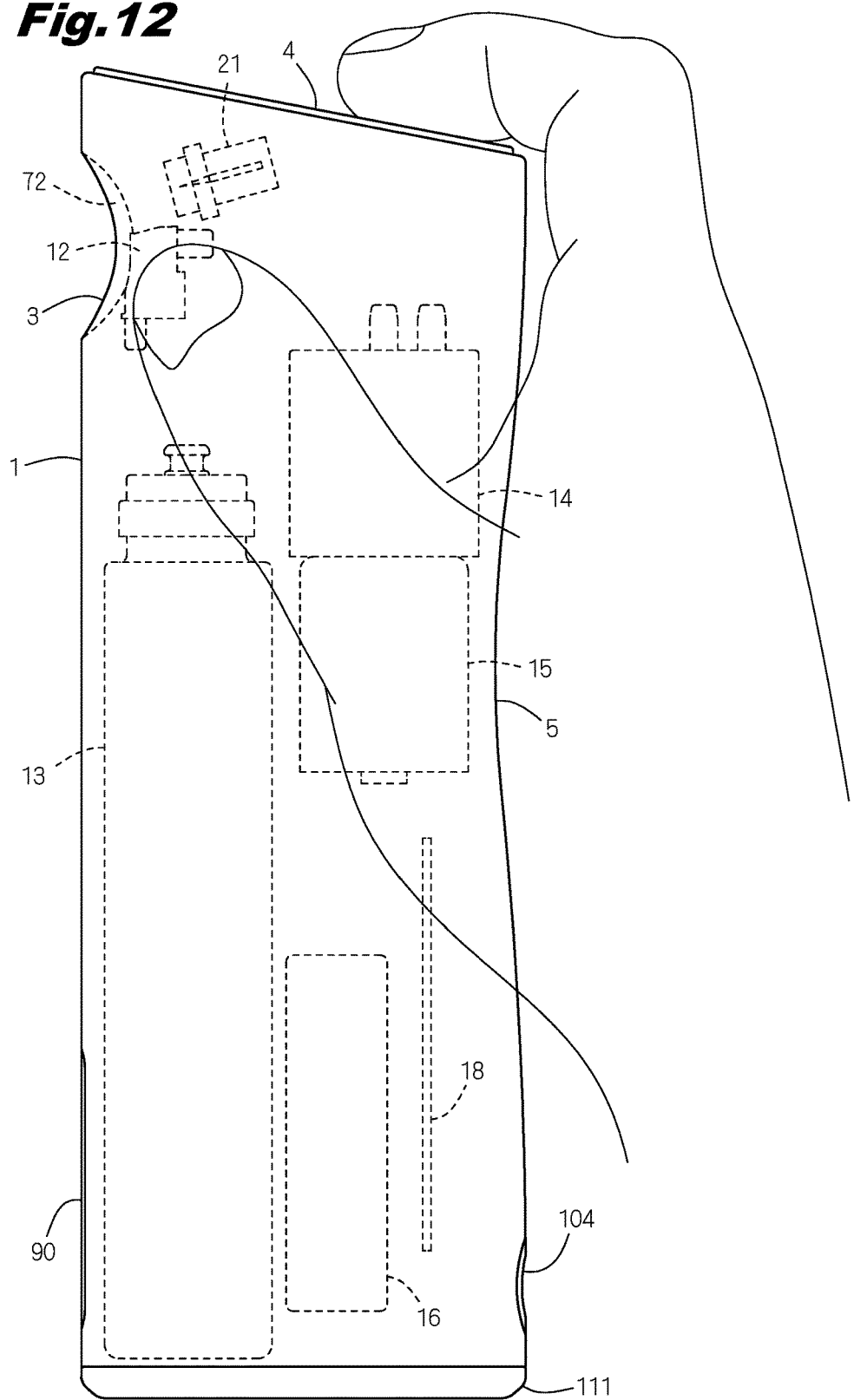

SPRAYER

TECHNICAL FIELD

The present invention relates to a sprayer used as a cosmetic mist device for spray-dispensing mist of lotion for facial skin or hair or mist of beauty serum for hair or as an inhaler for spray-dispensing mist of medicinal solution into a throat and a mouth cavity. The sprayer includes an air pump, a motor and a battery for driving the pump, a mist nozzle, and a tank for storing a mist liquid concentrate.

BACKGROUND ART

There is a known sprayer of this type as disclosed in Patent Document 1, for example. Here, a vertical cylinder portion and a lateral cylinder portion form a main body case in an L shape, a diaphragm pump and a motor for driving the pump are housed in the vertical cylinder portion, and a battery is housed behind the motor. A mist nozzle is disposed in the lateral cylinder portion and a nozzle retaining cylinder covering a periphery of the mist nozzle is supported by the lateral cylinder portion to be able to come in and out. A tank (medicinal solution tank) is detachably mounted to a squinch-shaped tank mounting portion formed by a front face of the vertical cylinder portion and a lower face of the lateral cylinder portion. The diaphragm pump is driven for reciprocation by an eccentric cam fixed to an output shaft of the motor to supply pressurized air to the mist nozzle and send the mist of medicinal solution out to the nozzle retaining cylinder by Venturi effect in the mist nozzle. The sprayer in Patent Document 1 is formed as a relatively small spray inhaler for spray-dispensing saline solution or medicinal gargle solution stored in the tank into a throat and a mouth cavity and therefore the tank is as small as a relatively large a few-centimeter ice cube.

Patent Document 2 discloses a similar sprayer (inhaler) which is similar to the sprayer in Patent Document 1 in that a diaphragm pump and a motor are housed in a main body case and that a mist nozzle and a tank are disposed forward of the pump and the motor. Specifically, an inner case is housed in the main body case, the mist nozzle, the diaphragm pump, and the motor are mounted in the inner case, and the tank (liquid supply tank) is detachably mounted to the inner case. A spray central axis of the mist nozzle is inclined diagonally upward and the diaphragm pump is mounted to a vertical wall of the inner case positioned behind the mist nozzle. The diaphragm pump is driven for reciprocation by an eccentric cam fixed to an output shaft of the motor to feed pressurized air to the mist nozzle, form water or medicinal solution drawn up from the tank by Venturi effect in the mist nozzle into mist, and send the mist out to a spray cylinder. In a lower portion of the main body case, a pair of front and back batteries is housed.

PRIOR ART DOCUMENTS

Patent Documents

Patent Document 1: Japanese Utility Model Application Publication No. S62-09872 (lines 4 to 25 in a right column on page 1, FIG. 4)

Patent Document 2: Japanese Patent Application Publication No. S58-44029 (lines 11 to 23 in a left column on page 2, FIG. 6)

SUMMARY OF THE INVENTION

Problems to be Solved by the Invention

In the sprayer in Patent Document 1, because heavy objects such as the motor, the battery, and the tank are disposed in parallel on front and back sides in a lower half portion of the main body case, a position of the center of gravity of the spray inhaler is low and the spray inhaler can be placed in a stable state on a placing face. Moreover, although a capacity of the tank of the spray inhaler is small, it is no problem as long as the spray inhaler is used as an inhaler from which a low dose of medicinal solution is consumed at a time.

However, in order to spray mist of lotion or water to facial skin or to spray-dispense mist of beauty serum for hair or water to hair, a larger amount of lotion or beauty serum is consumed than when the sprayer is used as the inhaler and therefore the tank inevitably becomes empty in a short time and it is necessary to frequently replenish the lotion or the water. The sprayer in Patent Document 2 involves similar inconvenience. Furthermore, under present circumstances, a commercially available portable lotion mist device has an even smaller tank capacity and it is necessary to use specific lotion with low viscosity. Therefore, the mist device can be used temporarily at a workplace or the like but is not suitable for heavy use which consumes a large amount of lotion or water.

In order to resolve the above-described inconvenience, there is no choice but to increase the capacity of the tank. In this case, because it is unnecessary to increase the diaphragm pump and the motor in size similarly to the tank, only the tank of the sprayer is likely to be large. Moreover, the increase in the capacity of the tank causes the sprayer to lose weight balance, which is likely to gradually make a user to feel that the sprayer is heavier and to impair usability of the sprayer. Furthermore, female users having strong senses of beauty and insisting on and sticking to beauty are very unwilling to accept the sprayer with the tank simply increased in capacity as a cosmetic mist device. This is because the female users put much value on whether an external appearance design and an impression of an appearance are suitable to a cosmetic tool against their familiar cosmetic tools.

In the sprayer in Patent Document 2, because the main component members such as the mist nozzle, the diaphragm pump, the motor, and the tank are mounted in the inner case, the respective component members can be integrated with the inner case without variation in positional relationships. Moreover, because an air passage and a liquid passage are provided in the inner case, it is possible to generate the mist in a stable state. However, it is necessary to provide mounting portions adapted to the respective component members, which complicates an entire structure of the inner case. Furthermore, if a part of the inner case is damaged on drop impact, it is necessary to replace the entire inner case. Moreover, if a seal for the air passage or the liquid passage provided in the inner case deteriorates, it is necessary to disassemble the entire sprayer to replace the deteriorated seal and a series of replacement operations takes much work and is expensive.

It is an object of the present invention to provide a sprayer which can be used as a medial inhaler and a cosmetic mist device and also includes a tank of a large capacity enough to dispense mist with a sufficient remaining amount of liquid even in heavy use of the sprayer.

It is an object of the present invention to provide a sprayer which has excellent usability with an impression suitable to a cosmetic mist device, even if the sprayer includes a large-capacity tank.

It is an object of the present invention to provide a sprayer in which a mist nozzle and an air pump disposed at separate positions from each other are connected properly so that mist can be generated appropriately and in which a case structure mounted with component members such as the mist nozzle and the air pump is simplified so that mounting of respective component parts and replacement of parts can be carried out easily with less work.

Solutions to the Problems

A sprayer according to an aspect of the present invention includes: an air pump 14; a motor 15 and a battery 16 for driving the pump 14; a mist nozzle 12; a tank 13 for storing a mist liquid concentrate; and a cylindrical main body case 1 for housing these respective devices. A mist opening 3 is open in an upper portion of a front wall 1a of the main body case 1 and the mist nozzle 12 is disposed on an inner side of the mist opening 3. The air pump 14 for supplying pressurized air to the mist nozzle 12, the motor 15 for driving the pump 14, and an electrical component section 17 including the battery 16 are disposed on a back half side in the main body case 1. The tank 13 extending from a bottom portion of the main body case 1 to a position below the mist nozzle 12 is detachably housed on a front half side in the main body case 1.

Figure 14:
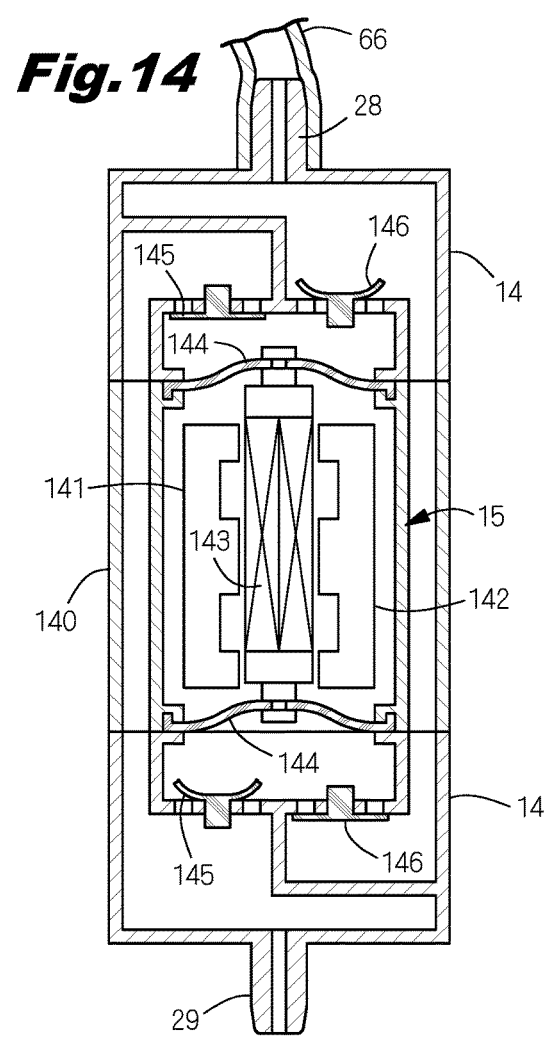
Figure 15:
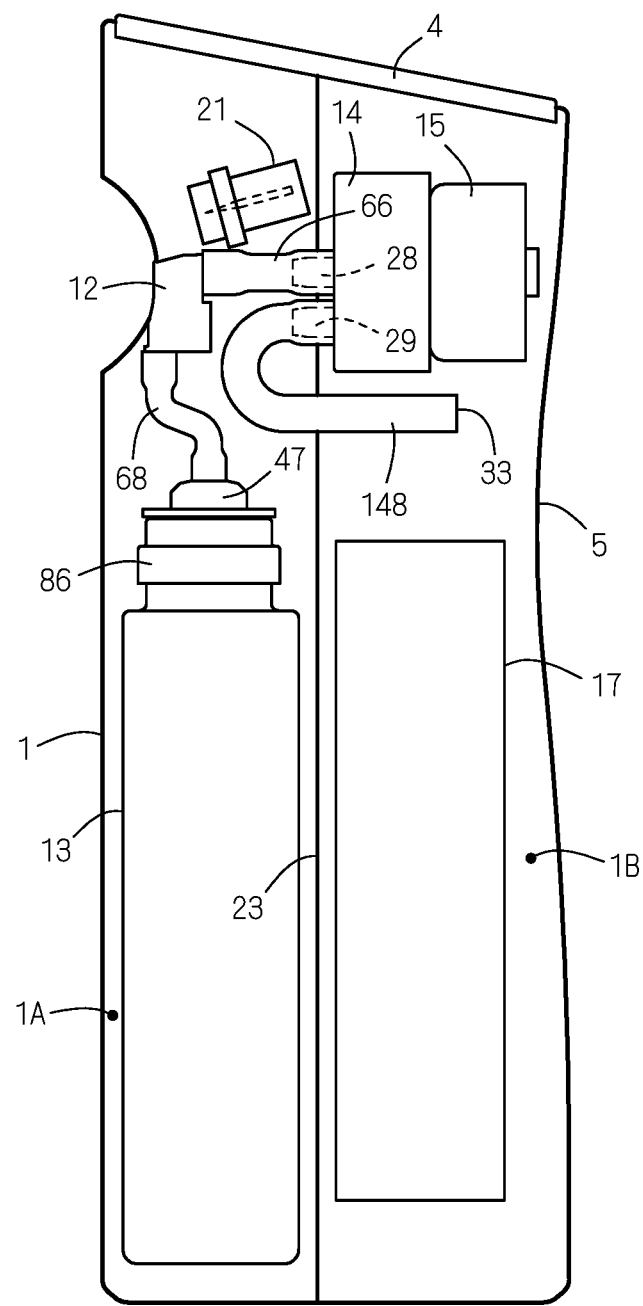

The mist nozzle 12 and the tank 13 are disposed on the front half side in the main body case 1 and the air pump 14, the motor 15, and the electrical component section 17 are disposed on the back half side in the main body case 1. The tank 13 is formed to be vertically long so that an upper end of the tank 13 reaches a middle portion in a vertical direction of the air pump 14. An air pump 14 and a motor 15 may be disposed to be adjacent to each other in a vertical direction as shown in FIG. 1 or each of the air pumps 14 may be disposed above and below a motor 15 as shown in FIG. 14. Moreover, an air pump 14 and a motor 15 may be arranged in a front-back direction as shown in FIG. 15, if necessary.

The air pump 14, the motor 15, and the electrical component section 17 are disposed in this order from above on the back half side in the main body case 1.

An inside of the main body case 1 is divided into a front chamber 1A on a front side and a back chamber 1B on a back side by a division wall 23 continuous in the vertical direction. The tank 13 is housed in the front chamber 1A, and the air pump 14, the motor 15, and the electrical component section 17 including the battery 16 are housed in the back chamber 1B.

When a front-back width in the front chamber 1A is B1 and a front-back width in the back chamber 1B is B2, the front-back width B2 in the back chamber 1B is set to be larger than the front-back width B1 in the front chamber 1A.

A coupling member 47 to which a connection portion 86 provided to an upper portion of the tank 13 is to be connected is fixed to an upper end of the front chamber 1A. A positioning portion 135 for receiving a peripheral face of the tank 13 and positioning the connection portion 86 with respect to the coupling member 47 is formed on an inner face of an upper portion of the front chamber 1A.

An upper portion of the division wall 23 is brought closer to the front wall 1a of the main body case 1 than the other portion of the division wall 23 so as to form the positioning portion 135 integrally with the division wall 23.

A bottom lid 111 for opening and closing a bottom opening of the main body case 1 is provided to a lower end of the main body case 1. The bottom lid 111 is formed in a plate shape including an endless ring-shaped lid peripheral edge wall 112 and open upward. A liquid receiving recessed portion 115 for receiving the mist liquid concentrate leaking from the tank 13 is formed in an annular shape on an inner face of the bottom lid 111.

An inner bottom wall 24 for closing a lower opening of the back chamber 1B is fixed to the lower end of the main body case 1 and a socket holder 103 for supporting a connector 20 is fixed to an upper face of the inner bottom wall 24. A lock mechanism for locking and retaining the bottom lid 111 mounted to the main body case 1 is provided between the bottom lid 111 and the inner bottom wall 24. The lock mechanism includes an operating knob 113 disposed on a lower face side of the bottom lid 111, an engagement arm 119 provided to the operating knob 113 and protruding above the bottom lid 111, and a lid engagement frame 120 provided to a lower face side of the inner bottom wall 24. A plug-shaped protrusion 124 provided to a lower face of the socket holder 103 is engaged in a removal hole 123 open in the inner bottom wall 24 to correspond to a position where the lid engagement frame 120 is formed, so that the plug-shaped protrusion 124 closes the removal hole 123.

The main body case 1 is formed to have an elliptic section having a long axis in the front-back direction. A switch operating member 4 for switching a switch 48 for activating the motor 15 is disposed at an upper end of the main body case 1. A grip portion 5 for receiving a user's palm is formed in a recessed manner near an upper portion of a back face of the main body case 1. The air pump 14 and the motor 15 are disposed in the back chamber 1B facing the grip portion 5.

An air supply opening 60 of the mist nozzle 12 and a discharge portion 28 of the air pump 14 are connected via an air supply tube 66. A liquid supply opening 62 of the mist nozzle 12 and an outlet portion 93 of the coupling member 47 are connected via the liquid supply tube 68. An intake port 33 of an intake portion 29 of the air pump 14 is positioned behind the discharge portion 28.

A sprayer according to another aspect of the present invention includes: a mist nozzle 12; a tank 13 for storing a mist liquid concentrate; an air pump 14; a motor 15 and a battery 16 for driving the pump 14; and a main body case 1 for housing these respective devices. The mist nozzle 12 is supported by a nozzle case 11 fixed in the main body case 1. An air supply opening 60 of the mist nozzle 12 and a discharge portion 28 of the air pump 14 are connected via an air supply tube 66.

The nozzle case 11 is formed by a left case body 11L and a right case body 11R which are two parts divided in a left-right direction and the mist nozzle 12 is pinched and fixed by both the case bodies 11L, 11R. A middle portion of the air supply tube 66 is pinched and fixed by a retaining hole 43 provided in a junction between the left case body 11L and the right case body 11R so as not to move freely.

The nozzle case 11 is mounted to an upper portion in the main body case 1. A switch operating member 4 for switching a switch 48 for the motor 15 is disposed above the main body case 1. An upper wall 41 of the nozzle case 11 serves also as a switch base for supporting the switch operating member 4.

A seal body 100 for sealing a switch window 42, which is open in the upper wall 41 of the nozzle case 11, in a watertight manner is mounted to an opening edge of the switch window 42. A switching operation by the switch operating member 4 is transmitted to the switch 48 via the seal body 100.

A coupling member 47 to which a connection portion 86 provided to an upper portion of the tank 13 is to be connected is fixed to a lower end of the nozzle case 11. The mist nozzle 12 and the coupling member 47 are connected via a liquid supply tube 68. Bent passage portions 70 are formed at two positions of a middle portion of the liquid supply tube 68 so that a center of a connection between the mist nozzle 12 and the liquid supply tube 68 is positioned forward of a center of a connection between the coupling member 47 and the liquid supply tube 68.

Partition walls 35 crossing the air supply tube 66 are provided to the left case body 11L and the right case body 11R. The retaining hole 43 and a tube support wall 44 for supporting the middle portion of the air supply tube 66 are formed at a junction of the partition walls 35. The tube support wall 44 guides the middle portion of the air supply tube 66 in a curved manner to retain a bent portion 69 of the air supply tube 66 in a predetermined shape.

An electrical component case 10 is disposed below a back portion of the nozzle case 11. The air pump 14 and the motor 15 are mounted to an upper portion of the electrical component case 10.

The air pump 14, the motor 15, the battery 16, and a circuit board 18 are mounted to the electrical component case 10. A fastening member 102 fastens the left case body 11L and the right case body 11R while both the case bodies 11L, 11R pinch a plurality of positions of the upper portion of the electrical component case 10 to thereby integrate the electrical component case 10 and the nozzle case 11 into an actuation unit 2. The actuation unit 2 is detachably inserted and mounted into the main body case 1.

Effects of the Invention

In the sprayer according to one aspect of the present invention, the main body case 1 is formed in the cylindrical shape and the mist nozzle 12 is disposed on the inner side of the mist opening 3 open in the upper portion of the front wall 1a of the main body case 1. The air pump 14, the motor 15, and the electrical component section 17 including the battery 16 are disposed on the back half side in the main body case 1 and the tank 13 is detachably housed on the remaining front half side. The tank 13 is formed into the vertically long structure extending from the bottom portion of the main body case 1 to the position below the mist nozzle 12 to achieve the large capacity. Therefore, it is possible to provide the sprayer capable of continuously dispensing the mist with a sufficient remaining amount of liquid even in heavy use which consumes a large amount of mist.

Moreover, because the tank 13 is formed in the vertically long structure to thereby be increased in capacity within the space in the main body case 1, it is possible to prevent the increase in capacity of the tank 13 from impairing the external appearance design of the main body case 1. Especially when the sprayer is used as a cosmetic mist device, the external appearance design and an impression of an appearance can give an impression suitable to a cosmetic tool, though the sprayer has the large-capacity tank 13. The sprayer can be used as a medical inhaler or the cosmetic mist device.

If the tank 13 is formed to be vertically long so that the upper end of the tank 13 reaches the middle portion in the vertical direction of the air pump 14, the tank 13 can obtain further increased capacity to thereby be able to continuously dispense the mist with the sufficient remaining amount of liquid. Furthermore, because the mist liquid concentrate is stored in the tank 13 which is vertically long so that the upper end of the tank 13 reaches the middle portion in the vertical direction of the air pump 14, it is possible to suppress large changes in a liquid level of the mist liquid concentrate and sloshing of the mist liquid concentrate in the front-back and right-left directions even in spraying the mist while moving the sprayer widely. Therefore, it is possible to continuously spray the mist in a stable state and also it is possible to hold the sprayer in the stable state without being affected by the sloshing of the mist liquid concentrate.

If the air pump 14, the motor 15, and the electrical component section 17 are disposed in this order from above on the back half side in the main body case 1, it is possible to dispose the respective devices in an orderly manner while effectively and economically using a space on the back half side in the main body case 1. Therefore, it is possible to achieve a slim impression of the external appearance of the main body case 1 while preventing the main body case 1 from unlimitedly increasing in size in the front-back direction or the right-left direction.

If the tank 13 is housed in the front chamber 1A defined by the division wall 23 and the air pump 14, the motor 15, and the electrical component section 17 including the battery 16 are housed in the back chamber 1B, it is possible to prevent the mist liquid concentrate leaking from the tank 13 from flowing into the back chamber 1B with the division wall 23. Therefore, it is possible to satisfactorily prevent failure of an electrical system such as a short circuit and heat generation caused by adhesion of the leaked mist liquid concentrate to the electrical devices housed in the back chamber 1B. Even if the main body case 1 placed in a vertically long attitude is accidentally knocked over and the mist liquid concentrate leaks out of the tank 13 on impact, it is possible to prevent the mist liquid concentrate from immediately flowing into the back chamber 1B with the division wall 23 to thereby satisfactorily prevent failure of the electrical devices. The division wall 23 functions also as a reinforcing structure for the main body case 1 formed in the vertically long cylindrical shape and contributes to increase in structural strength of the main body case 1. Therefore, even if a strong drop impact or the like acts on the main body case 1, it is possible to satisfactorily prevent damage to the main body case 1.

The front-back width B2 of the back chamber 1B is set to be larger than the front-back width B1 of the front chamber 1A, because the air pump 14, the motor 15, and the electrical component section 17 having larger diameters (or front-back widths) than the tank 13 need to be housed in the roomy back chamber 1B. By disposing the air pump 14 at the upper portion in the back chamber 1B, it is possible to decrease an entire length of the air supply tube 66 for connecting the mist nozzle 12 and the air pump 14 to thereby minimize passage resistance and therefore it is possible to efficiently send the pressurized air to the mist nozzle 12.

If the positioning portion 135 is provided on the inner face of the upper portion of the front chamber 1A, the positioning portion 135 can receive the peripheral face of the tank 13 inserted and mounted into the front chamber 1A to thereby appropriately position the connection portion 86 of the tank 13 with respect to the coupling member 47. Therefore, by simply inserting the tank 13 into the front chamber 1A, it is possible to align the center of the connection portion 86 of the tank 13 which is formed to be vertically long with the center of the cylindrical wall 92 of the coupling member 47 at an upper end position in the front chamber 1A to thereby easily connect the vertically long tank 13 to the coupling member 47.

If the upper portion of the division wall 23 is brought closer to the front wall 1a of the main body case 1 than the other portion of the division wall 23 so as to form the positioning portion 135 integrally with the division wall 23, it is possible to form the positioning portion 135 without affecting the external appearance of the main body case 1. Although the positioning portion 135 can be formed on the front wall 1a or a peripheral wall of the main body case 1 to position the tank 13 with respect to the coupling member 47, a molding strain such as a sink mark is formed in this case on an outer face of the portion where the positioning portion 135 is formed to thereby impair the external appearance of the main body case 1. By bringing the upper portion of the division wall 23 close to the front wall 1a, the front-back width of the back chamber 1B is increased and the larger air pump 14 can be disposed in an upper portion in the back chamber 1B.

If the bottom lid 111 is formed in the plate shape including the lid peripheral edge wall 112 and open upward and the liquid receiving recessed portion 115 is formed in the annular shape on the inner face of the bottom lid 111, the liquid receiving recessed portion 115 can receive the mist liquid concentrate to prevent the mist liquid concentrate from leaking out of the main body case 1 even if the mist liquid concentrate leaks from the tank 13 for any cause.

If the lock mechanism for the bottom lid 111 is formed by the operating knob 113, the engagement arm 119, the lid engagement frame 120, and the like and the plug-shaped protrusion 124 is engaged in the removal hole 123 open in the inner bottom wall 24 to close the removal hole 123, it is possible to prevent the mist liquid concentrate received by the bottom lid 111 from entering the back chamber 1B through the removal hole 123. Therefore, it is possible to reliably prevent the failure of the electrical system such as the short circuit caused by adhesion of the mist liquid concentrate leaked from the tank 13 to the electrical component section 17 disposed in a lower space in the back chamber 1B. Moreover, by engaging the plug-shaped protrusion 124 provided to the lower face of the socket holder 103 in the removal hole 123 in the inner bottom wall 24, backlash of the socket holder 103 in the front-back direction can be prevented and therefore it is possible to appropriately attach and detach the charging plug to and from the connector 20.

If the grip portion 5 for receiving the user's palm is formed in the recessed manner near the upper portion of the back face of the main body case 1 and the air pump 14 and the motor 15 are disposed in the back chamber 1B facing the grip portion 5, the user can lightly spray the mist while firmly gripping the sprayer. This is because, gripping of the main body case 1 with the user's palm placed on the grip portion 5 allows the user to lightly spray the mist while holding the main body case 1 with the heavy air pump 14 and motor 15 positioned close to the user's palm and without gradually feeling that the sprayer is heavier. Because the user's palm is received by the grip portion 5 which is recessed inward, it is possible to reliably prevent displacement of the hand in the vertical and peripheral directions when the user sprays the mist while moving the sprayer widely to thereby improve usability.

If the intake port 33 of the intake portion 29 is positioned behind the discharge portion 28, it is possible to prevent forming of negative pressure in a space around the intake portion 29 during actuation of the air pump 14 and the negative pressure from affecting the mist nozzle 12. Therefore, the mist nozzle 12 can effectively generate the mist.

In the sprayer according to another aspect of the present invention, the mist nozzle 12 is supported by the nozzle case 11 fixed in the main body case 1 and the discharge portion 28 of the air pump 14 and the air supply opening 60 of the mist nozzle 12 disposed in the main body case 1 are connected via the air supply tube 66. If the mist nozzle 12 and the air pump 14 disposed at separate positions from each other are connected via the air supply tube 66 in this manner, the mist nozzle 12 and the air pump 14 can be properly connected via the air supply tube 66 of the same tube length, even if there is small variation in positional relationships between the mist nozzle 12 and the air pump 14. Therefore, it is possible to achieve a constant flow of pressurized air sent from the air pump 14 to the mist nozzle 12 to thereby appropriately generate the mist. Moreover, because the mist nozzle 12 is supported by the nozzle case 11 fixed in the main body case 1, it is possible to simplify the structure of the nozzle case 11 as compared with the conventional sprayer in which the main component members such as the mist nozzle, the diaphragm pump, the motor, and the tank are mounted in the inner case.

If the nozzle case 11 is formed by the left and right case bodies 11L, 11R, if the mist nozzle 12 is pinched and fixed by both the case bodies 11L, 11R, and if the middle portion of the air supply tube 66 is pinched and fixed by the retaining hole 43 provided in the junction between both the case bodies 11L, 11R, it is possible to constantly maintain a certain positional relationship between the mist nozzle 12 and the air supply tube 66. Therefore, it is possible to achieve the constant flow of pressurized air sent from the air pump 14 so that the mist nozzle 12 can generate the mist in the stable state.

If the switch operating member 4 is disposed above the main body case 1, it is possible to obtain a simpler external appearance of the sprayer than when a switch operating member 4 is disposed on a peripheral face of a main body case 1. Especially when the sprayer is used as a cosmetic mist device, it is possible to simplify an impression of an appearance to thereby give an impression suitable to the cosmetic mist device. Moreover, if the switch operating member 4 is supported by the upper wall 41 of the nozzle case 11, it is unnecessary to provide a support structure for the switch operating member 4 to an upper portion of an inner face of the main body case 1, which simplifies an inner face structure of the main body case 1. As a result, in forming the main body case 1 into the vertically long cylindrical shape, it is possible to simplify a structure of a metal mold for molding to facilitate molding of the main body case 1.

If the switch window 42 is open in the upper wall 41 of the nozzle case 11 and the seal body 100 is mounted to the opening edge of the switch window 42 to seal the window 42 in the watertight manner, the seal body 100 can prevent entry of water droplets, dust, or the like into the nozzle case 11 through the switch window 42. Therefore, it is possible to completely prevent adhesion of the water droplets and the dust to the switch 48, a switch board, and the like disposed in the nozzle case 11 to thereby prevent a short circuit or a malfunction of the switch 48.

If the bent passage portions 70 are formed at the two positions of the middle portion of the liquid supply tube 68 so that the center of the connection between the mist nozzle 12 and the liquid supply tube 68 is positioned forward of the center of the connection between the coupling member 47 and the liquid supply tube 68, it is possible to apply flow resistance to the mist liquid concentrate flowing in the bent passage portions 70. This is because a flowing direction of the mist liquid concentrate is forcibly changed every time the mist liquid concentrate passes through the bent passage portion 70 and the flow resistance acts on the mist liquid concentrate every time the flowing direction is changed. Moreover, the increase in the flow resistance can reduce a flow velocity of the mist liquid concentrate drawn up into the mist nozzle 12 due to negative pressure to thereby prevent the mist from being sprayed diagonally upward from the nozzle hole 57 in an initial state of spraying of the mist. Furthermore, the nozzle hole 57 of the mist nozzle 12 can be brought further forward in the main body case 1 over a distance corresponding to bending of the liquid supply tube 68 in a crank shape so that the total amount of mist generated by the mist nozzle 12 can be ejected to the object on which the mist is to be sprayed.

If the retaining hole 43 and the tube support wall 44 for supporting the middle portion of the air supply tube 66 are formed at the junction of the partition walls 35 of the left and right case bodies 11L, 11R, the tube support wall 44 can guide the middle portion of the air supply tube 66 in the curved manner to thereby retain the bent portion 69 of the air supply tube 66 in the predetermined shape. Moreover, because the tube support wall 44 supports the middle portion of the air supply tube 66, it is possible to reliably prevent the air supply tube 66 from swinging synchronously with fluctuations in discharge pressure of the air pump 14, even if the discharge pressure periodically fluctuates. Therefore, it is possible to achieve the constant flow of pressurized air sent from the air pump 14 to the mist nozzle 12 through the air supply tube 66 so that the mist nozzle 12 can generate the mist in the further stable state.

If the electrical component case 10 is disposed below the back portion of the nozzle case 11 and the air pump 14 and the motor 15 are mounted to the upper portion of the electrical component case 10, it is possible to naturally simplify case structures of the electrical component case 10 and the nozzle case 11 housed in the main body case 1. Therefore, it is possible to easily carry out mounting of the air pump 14, the motor 15, and the like to the electrical component case 10, mounting of the mist nozzle 12, the air supply tube 66, and the like in the nozzle case 11, and replacement of the parts with less work.

If the fastening member 102 integrates the electrical component case 10 and the nozzle case 11 into the actuation unit 2, it is possible to easily mount most of the parts including the mist nozzle 12, the air pump 14, and the motor 15 in the respective cases 10, 11 outside the main body case 1. Moreover, by inserting and mounting the actuation unit 2 into the main body case 1 and then fixing the actuation unit 2, it is possible to integrate most of the parts excluding the tank 13 with the main body case 1, which reduces a series of steps required to assemble the sprayer. Furthermore, because most of the parts can be taken out of the main body case 1 by detaching the actuation unit 2 from the main body case 1, it is possible to simplify disassembly operation and reassembly operation for replacing the parts.

BRIEF DESCRIPTION OF THE DRAWINGS

FIG. 1 is a vertical sectional side view of a cosmetic mist device.

FIG. 2 is an explanatory diagram showing a diagrammatic sketch of the cosmetic mist device.

FIG. 3 is an exploded side view of an actuation unit.

FIG. 4 is a vertical sectional side view of an upper structure of the cosmetic mist device.

FIG. 5 is a front view of the cosmetic mist device.

FIG. 6 is a vertical sectional side view of a lower structure of the cosmetic mist device.

FIG. 7 is a sectional view along line A-A in FIG. 6.

FIG. 8 is a vertical sectional side view of a state in the middle of assembly of the actuation unit.

FIG. 9 is a sectional view along line B-B in FIG. 1.

FIG. 10 is a sectional view along line C-C in FIG. 1.

FIG. 11 is an explanatory diagram showing a diagrammatic sketch of a configuration structure of electrical components of the cosmetic mist device.

FIG. 12 is a side view of a used state of the cosmetic mist device.

FIG. 13 is a sectional view of a main part of an embodiment formed by changing a part of an air pump.

FIG. 14 is a sectional view of another embodiment of the air pump.

FIG. 15 is a conceptual diagram showing another embodiment of a sprayer.

MODES FOR CARRYING OUT THE INVENTION

Embodiment

FIGS. 1 to 12 show an embodiment in which a sprayer according to the present invention is applied to a cosmetic mist device (hereafter simply referred to as "mist device"). In the present invention, "front", "back", "left", "right", "up", and "down" conform to crossed arrows shown in FIGS. 1 and 5 and indications, "front", "back", "left", "right", "up", and "down" shown close to the respective arrows.

In FIGS. 1 and 2, the mist device is formed by a vertically long cylindrical main body case 1 as a basic structure which is open on upper and lower sides and in which an actuation unit 2 is housed. The main body case 1 has an elliptic section having a long axis in a front-back direction and a left-right width which is set to be sufficiently smaller than a front-back width so as to fit comfortably in hands of women (who are main users) and also the main body case 1 is of such size as to be easy to hold with one hand. In the embodiment, if the front-back width of the main body case 1 is about 65 mm, the left-right width is 45 mm. A circular mist opening 3 is open in an upper portion of a front wall 1*a* of the main body case 1 and a switch knob (switch operating member) 4 is disposed at an upper end (upper portion) of the main body case 1. A grip portion 5 is formed in a gently recessed shape near an upper portion of a back face of the main body case 1 (see FIG. 1). In FIG. 2, a reference sign 6 denotes a cap and the mist opening 3 and an outer face of the switch knob 4 are covered with the cap 6 in a state in which the cap 6 is put on the main body case 1 when the mist device is not used. In this way, it is possible to prevent turning on of the switch knob 4 by mistake. Moreover, it is possible to prevent dust from adhering to a nozzle hole 57 of a mist nozzle 12 or an area around the nozzle hole 57 or foreign matter from entering the nozzle hole 57 to clog it. Moreover, the cap 6 functions also as a protector when the mist device is dropped on a floor face or the like and contributes to prevention of damage to devices disposed to face an inner face of the cap 6.

As shown in FIG. 3, the actuation unit 2 has a framework formed by a vertically long electrical component case 10 and an inverted L-shaped nozzle case 11 mounted to an upper portion of the electrical component case 10 and is formed by mounting component parts of a mist generating structure and an ion generating structure to both the cases 10, 11. The mist generating structure is formed by the mist nozzle 12 disposed at a center of an inner side of the mist opening 3, a tank 13 disposed below the nozzle 12, an air pump 14, a motor 15 for driving the pump 14, an electrical component section 17 including a secondary battery (battery) 16, and the like. The electrical component section 17 is provided with a circuit board 18 mounted with a control circuit, a resin mold 19, a connector 20 for charging, the above-mentioned secondary battery 16, an auxiliary circuit board 22, and the like.

The ion generating structure is formed by the above-mentioned resin mold 19, an electrode unit 21 disposed above the mist nozzle 12, the auxiliary circuit board 22, and the like. A preceding group of circuits for current regulation is mounted on the auxiliary circuit board 22 and a following circuit for current regulation is sealed in the resin mold 19. The auxiliary circuit board 22 is disposed in a space beside the secondary battery 16 and fixed to the electrical component case 10.

In order to mount the above-described respective devices in the main body case 1 in an orderly manner, an inside of the main body case 1 is divided into a front chamber 1A and a back chamber 1B with a division wall 23 and the electrical component case 10 and the nozzle case 11 are further provided in the main body case 1. The division wall 23 is formed integrally with the main body case 1 and continuously extends from a position near a bottom opening to an upper position past a middle position in the main body case 1 along the front wall 1a in a vertical direction. An upper end of the division wall 23 supports a lower end wall of the nozzle case 11 and a lower end of the division wall 23 and the bottom opening of the main body case 1 cooperate to receive an inner bottom wall 24. The actuation unit 2 is fastened to the inner bottom wall 24 to integrate the actuation unit 2 and the main body case 1 with each other, which will be described later in detail.

If the tank 13 is housed in the front chamber 1A defined by the division wall 23 and the air pump 14, the motor 15, and the electrical component section 17 including the secondary battery 16 are housed in the back chamber 1B, the division wall 23 can prevent a mist liquid concentrate leaked from the tank 13 from flowing into the back chamber 1B. Therefore, it is possible to satisfactorily prevent failure of an electrical system such as a short circuit and heat generation caused by adhesion of the leaked mist liquid concentrate to the electrical devices housed in the back chamber 1B.

The electrical component case 10 is formed by a vertically long plastic molded article and cooperates with the main body case 1 to support the nozzle case 11 and an upper housing portion 25 for housing the air pump 14 and the motor 15 is formed at an upper half portion of the electrical component case 10 to be open backward. At a lower half portion of the electrical component case 10, a mold housing portion 26 and a battery housing portion 27 for housing the resin mold 19 and the secondary battery 16 are formed to be open forward. The circuit board 18 is disposed behind the mold housing portion 26 and the battery housing portion 27 and fixed to the electrical component case 10 and the auxiliary circuit board 22 is fixed in front of the circuit board 18. The connector 20 is fixed to a separately provided socket holder 103.

The air pump 14, the motor 15, the resin mold 19, and the secondary battery 16 are mounted to the electrical component case 10 in this order from above. While the air pump 14 and the motor 15 are mounted to the electrical component case 10 from a back face side, the resin mold 19 and the secondary battery 16 are mounted to the electrical component case 10 from a front face side.

As described above, the air pump 14, the motor 15, and the electrical component section 17 including the battery 16 are disposed in the back chamber (back half side) 1B in the main body case 1 and the vertically long tank 13 extending from a bottom portion of the main body case 1 to a position under the mist nozzle 12 is detachably housed in the front chamber (front half side) 1A in the main body case 1. An upper end of the tank 13 housed in the front chamber 1A reaches a middle portion in the vertical direction of the air pump 14. In this way, by increasing a capacity of the tank 13, it is possible to continuously dispense the mist with a sufficient remaining amount of liquid.

The air pump 14 is formed by a diaphragm pump and a discharge portion 28 and an intake portion 29 for introducing air into the pump protrude upward from an upper end of the air pump 14 to be adjacent to each other in the front-back direction. In the embodiment, a rolling pump in which the air pump 14 and the motor 15 are integrated with each other is employed. A plurality of diaphragms are provided in the rolling pump (air pump 14) and the air drawn in from the intake portion 29 is pressurized and sent out from the discharge portion 28 by vertically operating the diaphragms with drivers driven for rotation by the motor 15 to carryout "plate spinning motions".

As shown in FIG. 4, an intake port 33 of the intake portion 29 is positioned behind the discharge portion 28. In the embodiment, the intake portion 29 protruding upward is disposed behind the discharge portion 28 so that the intake port 33 in an upper end of the intake portion 29 is positioned behind the discharge portion 28. The three members, i.e., the mist nozzle 12, the discharge portion 28, and the intake portion 29 are disposed so that the discharge portion 28 is positioned behind the mist nozzle 12 and that the intake port 33 of the intake portion 29 is positioned behind the discharge portion 28. In this manner, the intake port 33 of the intake portion 29 is preferably provided in a position as far as possible from the mist nozzle 12. The point is that the intake port 33 has to be provided in such a position as to prevent negative pressure from affecting the mist nozzle 12, i.e., a position behind the discharge portion 28, because the negative pressure is likely to be formed in a space around the intake portion 29 due to the drawing in of the air from the intake portion 29.

As shown in FIG. 3, coupling protrusions 30 and 31 respectively having T-shaped sections are formed on a front portion of an upper face and an upper portion of a front face of the electrical component case 10 and paired left and right screw bosses 32 are formed to protrude downward from a lower end of the electrical component case 10. By supporting the nozzle case 11 on the front portion of the upper face and the upper portion of the front face of the electrical component case 10, coupling the nozzle case 11 to the electrical component case 10 with the coupling protrusions 30 and 31, and fastening both the cases 10 and 11 with a screw 102, it is possible to position the nozzle case 11 in the vertical, right-left, and front-back directions with respect to the electrical component case 10.

The nozzle case 11 is formed by a plastic molded article which is formed into a hollow case shape by a left case body 11L and a right case body 11R which are two parts divided in the left-right direction and an inside of the nozzle case 11 is divided into a front part and a back part by stepped partition walls 35 continuous with the division wall 23. A step portion 36 to be supported by the front portion of the upper face and the upper portion of the front face of the electrical component case 10 is formed on a lower face of a back portion of the nozzle case 11 to be orthogonal to the lower face and cut-away portions 37 and coupling recessed portions 38 to be engaged with the above-mentioned coupling protrusions 30 and 31 are respectively formed in lateral walls and vertical walls of the step portion 36. A mist window 39 is open in the front wall 1a of the nozzle case 11 to correspond to the mist opening 3 and a tank opening 40 to which the tank 13 is to be connected is open in a lower end wall.

An upper wall 41 covering an upper face of the nozzle case 11 is formed integrally with the left case body 11L and an oval switch window 42 is open at a center of the upper wall 41. A retaining hole 43 for pinching and fixing an air supply tube 66 (described later) and restricting movement of the air supply tube 66 is formed in a junction of the partition walls 35 and a tube support wall 44 for supporting a middle portion of the air supply tube 66 is formed in a partial arc shape (curved shape) along a lower edge of the retaining hole 43. A retaining hole 45 for pinching a peripheral face of the air supply tube 66 coupled to the discharge portion 28 and restricting movement of the air supply tube 66 is formed in a junction of the lateral walls of the step portion 36. A height position of a center of the retaining hole 43 is aligned with a height position of a center of a joint portion 58 (described later). The tube support wall 44 is formed integrally with the partition wall 35 of the left case body 11L.

As shown in FIG. 4, the mist nozzle 12, the electrode unit 21, and a coupling member 47 for the tank 13 are mounted in a section forward of the partition walls 35, a switch board is mounted in a section behind the walls 35, and a switch 48 for turning on and off energization of the motor 15 is mounted on an upper face of the switch board. L-shaped mounting protrusions 49 are formed to protrude from left and right side faces of the mist nozzle 12 (see FIG. 3) and the mist nozzle 12 can be integrated with the nozzle case 11 by engaging the mounting protrusions 49 with mounting frames 50 provided to inner side faces of the left and right case bodies 11L, 11R. Similar rectangular mounting protrusions 51, 52 are formed to protrude from left and right side faces of the electrode unit 21 and the coupling member 47 and the electrode unit 21 and the coupling member 47 can be integrated with the nozzle case 11 by engaging the protrusions 51, 52 with mounting frames 53, 54 provided to the inner side faces of the left and right case bodies 11L, 11R. A central axis of the electrode unit 21 fixed to the nozzle case 11 is tilted downward with respect to a horizontal spray central axis of the mist nozzle 12.

The mist nozzle 12 is formed by an injection molded article made of transparent plastic material, the nozzle hole 57 for ejecting the mist is open in a front face of an upper portion of the mist nozzle 12, and tubular joint portions 58 and 59 are respectively formed to protrude from a back face of the upper portion and a front portion of a lower face of the mist nozzle 12. The nozzle hole 57 faces an outer face of the main body case 1 through the mist opening 3. As shown in FIG. 4, an air supply opening 60 is open in the joint portion 58 on the back face of the upper portion and an air passage 61 tapered toward the nozzle hole 57 is formed to be continuous with the air supply opening 60. Similarly, a liquid supply opening 62 is open in the joint portion 59 at the front portion of the lower face and a liquid passage 63 tapered upward toward the nozzle hole 57 is formed to be continuous with the liquid supply opening 62.

The former joint portion 58 and the discharge portion 28 of the air pump 14 are connected via the air supply tube 66 in a shape of a side lying J and the latter joint portion 59 and an outlet portion 93 of the coupling member 47 are connected via a liquid supply tube 68 bent in a crank shape. The air supply tube 66 and the liquid supply tube 68 are respectively formed by soft and bendable tubes made of silicone rubber or plastic. In order to keep a certain bent shape of the air supply tube 66, the retaining hole 43 formed in the partition walls 35 crossing the air supply tube 66 pinches and fixes the middle portion of the air supply tube 66 so that the air supply tube 66 cannot move freely and the curved tube support wall 44 supports a lower face side of the air supply tube 66. Moreover, the retaining hole 45 formed in the junction of the lateral walls of the step portion 36 pinches and fixes the peripheral face of the air supply tube 66 coupled to the discharge portion 28. If the retaining hole 43 and the tube support wall 44 guide the middle portion of the air supply tube 66 in the curved state and the retaining hole 45 retains a lower portion of the air supply tube 66, it is possible to constantly keep a bent portion 69 formed at a tube path between the partition walls 35 and the discharge portion 28 in the certain shape as shown in FIG. 4.

The retaining hole 43 is formed by joining semicircular recesses formed in the partition walls 35 of the left and right case bodies 11L and 11R and the paired recesses pinch and support the air supply tube 66. Similarly, the retaining hole 45 is formed by joining semicircular recesses formed in the lateral walls of the step portion 36 of the left and right case bodies 11L and 11R and the paired recesses pinch and support the air supply tube 66. Each of the retaining holes 43 and 45 may be formed by forming a semi-oval recess in one of the case bodies 11L (or 11R) and not forming a recess in the other case body 11R (or 11L) to pinch the air supply tube 66. The point is that the air supply tube 66 is supported by the retaining holes 43 and 45. For example, the recessed shape of each of the holes may be a V shape, a trapezoidal shape, or a polygonal shape, for example. Furthermore, halved bosses may be integrally formed with the partition walls 35 and the lateral walls of the step portion 36, respectively, and retaining holes 43 and 45 formed on opposed faces of the bosses may retain and fix the air supply tube 66.

The liquid supply tube 68 connects the joint portion 59 of the mist nozzle 12 and the outlet portion 93 of the coupling member 47 while bent into the crank shape. Specifically, a center of a connection between the joint portion 59 of the mist nozzle 12 and the liquid supply tube 68 is positioned forward of a center of a connection between the outlet portion 93 of the coupling member 47 and the liquid supply tube 68 so that bent passage portions 70 are formed at two positions of a middle portion of the liquid supply tube 68. If the bent passage portions 70 are formed at the middle portion of the liquid supply tube 68 in this manner, it is possible to forcibly change a flowing direction of the mist liquid concentrate flowing in the bent passage portions 70 to apply flow resistance to the liquid concentrate. Moreover, the increase in the flow resistance reduces a flow velocity of the mist liquid concentrate drawn out of the upper end of the liquid passage 63 due to negative pressure to thereby prevent the mist from being sprayed diagonally upward from the nozzle hole 57 in an initial state of spraying of the mist. Furthermore, the nozzle hole 57 of the mist nozzle 12 can be brought further forward in the main body case 1 over a distance corresponding to bending of the liquid supply tube 68 in the crank shape. Moreover, if the air pump 14 is disposed at an upper end of the back chamber 1B and the mist nozzle 12 and the air pump 14 are connected via the air supply tube 66 bent in the J shape and having a short total length, it is possible to minimize passage resistance in the air supply tube 66 to thereby efficiently send the pressurized air sent out of the air pump 14 to the mist nozzle 12.

In order to close a clearance between a periphery of the nozzle hole 57 of the mist nozzle 12 and the mist opening 3, a mist opening cover 72 in a shape of a concave mirror is fitted in an inner face of the mist opening 3 and a mist emitting port 73 is open at a center of the cover 72 (see FIG. 5). An ionic species emitting window 74 is open above the mist emitting port 73 so that ion species generated in the electrode unit 21 can be emitted through the ionic species emitting window 74 toward a mist flow sprayed from the nozzle hole 57. Paired right and left engagement arms 75 are formed to protrude from an inner face of the mist opening cover 72 and the mist opening cover 72 is fixed to the nozzle case 11 by engaging the engagement arms 75 with paired engagement ribs 76 provided to the nozzle case 11 (see FIG. 10). The electrode unit 21 in this state is pinched and fixed in the right-left direction by the nozzle case 11 divided into the right and left two parts and the central axis of the electrode unit 21 is tilted in such an orientation as to intersect with a horizontal axis through the nozzle hole 57. A guard frame 77 for preventing a fingertip from touching the electrode unit 21 is provided on an inner face side of the ionic species emitting window 74 confronting a front end of the electrode unit 21. An LED 78 is disposed in close contact with a lower portion of a back face of the mist nozzle 12 and it is possible to turn on the LED 78 in ejection of the mist to thereby illuminate the mist flow with a soft light irradiated from the LED 78 and scattered by the mist nozzle 12.

In FIG. 4, the electrode unit 21 is formed by a plastic holder 80 formed in a cylindrical shape, a needle-shaped central electrode 81 fixed to a center of a front face of the holder 80, a ring-shaped opposite electrode 82 surrounding the central electrode 81, a dielectric cylinder 83 for insulating a space between both the electrodes 81 and 82, and the like. The central electrode 81 is connected to a diode 132 by a high-voltage lead and the opposite electrode 82 is connected to a ground lead 133 together with the switch knob 4 which serves also as a contact electrode (see FIG. 11). The ground lead 133 is connected to a ground line 134 of current regulating circuits for supplying high-voltage pulse current to the central electrode (discharge electrode) 81 and the opposite electrode 82.

The tank 13 is formed by a vertically long bottle-shaped tank main body 85 made of transparent or translucent plastic material, a connection portion 86 provided to an upper end of the tank main body 85, a suction pipe 87 in a shape of a straight pipe and fixed to a lower portion of an inner face of the connection portion 86, and the like. As shown in FIG. 9, the tank main body 85 has a section similar to a tunnel section. A cylindrical boss 88 to be inserted and coupled to the coupling member 47 is formed to protrude upward from a center of an upper face of the connection portion 86 and an O-ring 89 is mounted to a peripheral face of the cylindrical boss 88 (see FIG. 2).

As described previously, the main body case 1 has an elliptic section which is long in the front-back direction as shown in FIGS. 9 and 10 so that the main body case 1 fits comfortably in hands of women and is easy to hold with one hand. Moreover, the main body case 1 is formed in the vertically long cylindrical shape so as to have a simple external appearance. In order to achieve a large capacity of the tank 13 without impairing an impression of this external appearance of the main body case 1, the tank 13 has a long vertical length. To put it concretely, the tank 13 is formed to be vertically long so that the upper end of the tank main body 85 reaches the middle portion in the vertical direction of the air pump 14 positioned close to an upper portion of the back chamber 1B in a state in which the tank 13 is mounted in the front chamber 1A and the connection portion 86 of the tank 13 is coupled to the coupling member 47.

As described above, by forming the tank 13 into the vertically long structure to achieve the large capacity of the tank 13, it is possible to continuously dispense the mist with the sufficient remaining amount of liquid even in heavy use which consumes a large amount of mist. Moreover, because the mist liquid concentrate is stored in the vertically long tank 13, it is possible to suppress large changes in a liquid level of the mist liquid concentrate and sloshing of the mist liquid concentrate in the front-back and left-right directions even when a user sprays the mist while moving the mist device widely. Therefore, it is possible to continuously spray the mist in a stable state.

The tank 13 is a consumable item and sold with the tank main body 85 filled with the mist liquid concentrate in advance. Every time the mist liquid concentrate is consumed, the tank 13 is replaced with a new tank 13. As the mist liquid concentrate, lotion or water for providing moisture to facial skin, hair beauty serum for providing moisture to hair, and the like are available. In order to check a remaining amount level of the mist liquid concentrate, a transparent level check window 90 is provided to a lower portion of the front wall 1a of the main body case 1 (see FIGS. 1 and 5). By visually recognizing the remaining amount level in the tank main body 85 through the level check window 90, the user can know that it is soon necessary to prepare the new tank 13.

In order to connect the connection portion 86 of the tank 13 to the mist nozzle 12, the coupling member 47 is fixed to an upper end of the front chamber 1A and specifically a lower end wall of the nozzle case 11. A cylindrical wall 92 to which the connection portion 86 of the tank 13 is to be fitted over and mounted is formed to protrude downward from a lower face of the coupling member 47 and an outlet portion 93 to which the liquid supply tube 68 is to be connected is formed to protrude upward from an upper face of the coupling member 47. As shown in FIG. 4, when the connection portion 86 of the tank 13 is fitted over and mounted to the cylindrical wall 92 of the coupling member 47, the cylindrical boss 88 is fitted in a coupling hole (not shown) formed in the coupling member 47 and a clearance between the cylindrical boss 88 and the coupling member 47 is sealed with the O-ring 89. A lower portion of the coupling hole is tapered upward. Although it is not shown in the diagrams, a negative pressure preventing valve for preventing development of negative pressure in the tank main body 85 is provided in the connection portion 86.

In FIG. 4, the switch knob 4 is disposed on an upper face side of the upper wall 41 of the nozzle case 11 to close an opening in the upper end of the main body case 1, supported on the upper wall 41 to be able to swing up and down about a pin 98 provided to a lower face of a front portion of the switch knob 4, and pushed up and biased by a return spring (not shown). The switch knob 4 is formed by metal-plating a surface of a plastic molded article and a finger recessed portion 99 is formed in an upper face of the switch knob 4. An operating pin 101 for turning on and off the switch 48 with a seal rubber (seal body) 100 interposed therebetween is provided to a lower face of the switch knob 4. If the upper wall 41 of the nozzle case 11 serves also as a switch base for supporting the switch knob 4 as described above, it is unnecessary to provide brackets for supporting the pin 98 to the main body case 1, which facilitates molding of the main body case 1 formed into a vertically long cylindrical shape. The switch knob 4 is connected to the ground lead 133 and at the same potential as the opposite electrode 82 and the user touching the switch knob 4 is also at the same potential as the opposite electrode 82. Although it is not shown in the diagrams, a resistor with a large resistance is disposed between the ground line 134 and the switch knob 4. The switch knob 4 may be formed by using metal such as aluminum, copper, and a steel sheet as material.

The seal rubber 100 closes the switch window 42 formed in the above-mentioned upper wall 41 from the upper face side to prevent entry of water droplets, dust, or the like into the nozzle case 11. In an unused state, the switch knob 4 is inclined downward from a front portion toward a back portion of the opening along an upper opening plane of the main body case 1. If the switch knob 4 in this state is pressed down against elasticity of the return spring (not shown) and the seal rubber 100, the switch 48 is turned on. Because the switch 48 is a self-return switch, the motor 15 is activated only during the switch knob 4 is pressed down with an index finger and the motor 15 is deactivated when the holding down operation with the index finger is cancelled. As shown in FIG. 4, an O-ring 97 for coming in close contact with an inner wall of the main body case 1 is mounted to a periphery of the upper wall 41 of the nozzle case 11.

By mounting the nozzle case 11 mounted with the respective devices excluding the tank 13 to the electrical component case 10 mounted with the respective devices, the electrical component case 10 and the nozzle case 11 can be integrated to form the actuation unit 2. Specifically, the step portion 36 of the nozzle case 11 mounted with the respective devices is joined to a front upper corner of the electrical component case 10 mounted with the respective devices. Furthermore, by engaging the cut-away portions 37 and the coupling recessed portions 38 provided to the left and right case bodies 11L, 11R with the coupling protrusions 30, 31 of the electrical component case 10, both the cases 10 and 11 are positioned. By fastening the left and right case bodies 11L, 11R with the screw (fastening member) 102 in this state (see FIG. 4), the electrical component case 10 and the nozzle case 11 are integrated into the actuation unit 2. The air pump 14 and the motor 15 in this assembled state face the grip portion 5 with a back wall 1b interposed therebetween.

In order to fix the connector 20 formed in a shape of an earphone jack to the main body case 1, the socket holder 103 is pinched and fixed between the lower end of the electrical component case 10 and the inner bottom wall 24. As shown in FIGS. 6 and 7, the socket holder 103 has a base wall to be supported on the inner bottom wall 24 and an attachment portion 109 for the connector 20 is provided to an upper face of the base wall. Paired right and left plug-shaped protrusions 124 are formed on a lower face of a front portion of the base wall. The reason why the plug-shaped protrusions 124 are provided will be described later. By connecting a connector plug of a charger (not shown) to the connector 20, the secondary battery 16 can be charged.

Figure 8:
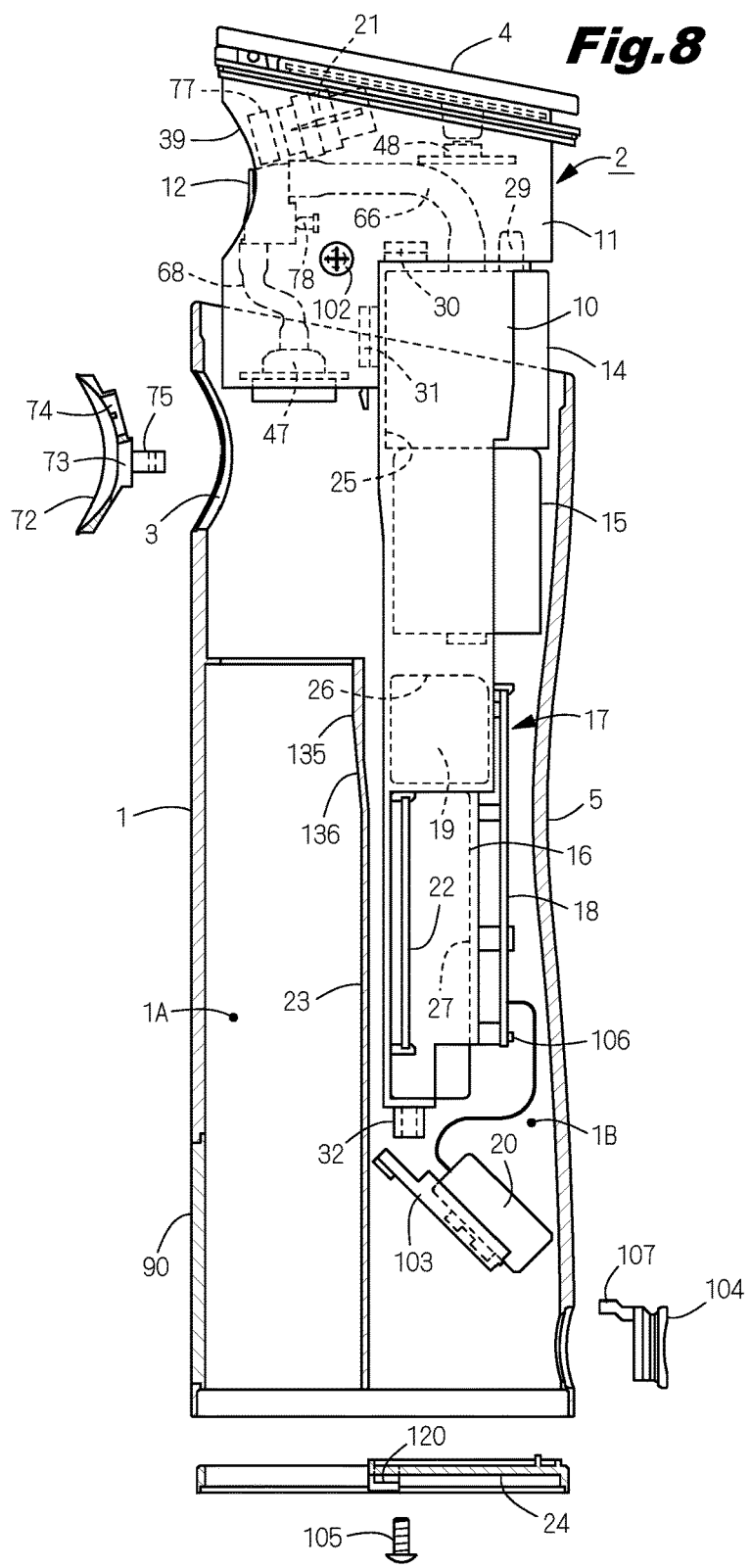
Figure 13:
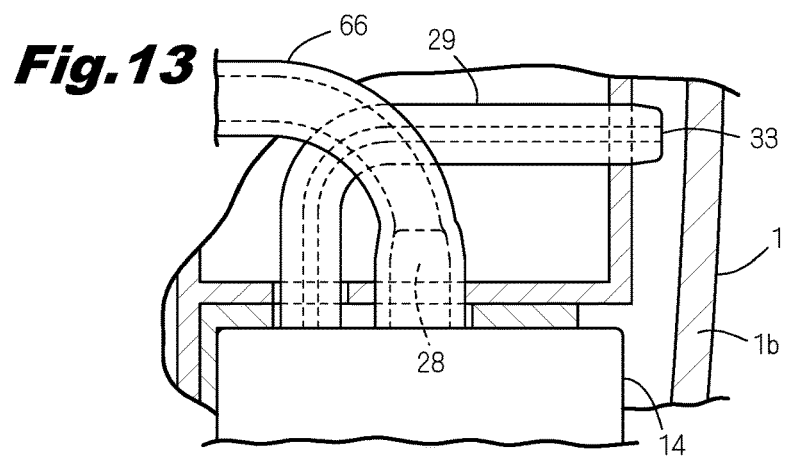

As shown in FIG. 8, the electrical component case 10 of the obtained actuation unit 2 is inserted and mounted into the back chamber 1B, the nozzle case 11 of the unit 2 is fitted in an upper portion of the front chamber 1A, and the lower end of the nozzle case 11 is brought in contact with the upper end of the division wall 23. In this state, the socket holder 103 is brought into a horizontal attitude and placed onto the lower end of the electrical component case 10 and an indicator ring 104 is fitted into a circular connector opening open in a lower portion of the back face of the main body case 1. Furthermore, by screwing a screw 105 down into a screw boss 32 of the electrical component case 10 in a state in which the inner bottom wall 24 is mounted into the bottom opening of the main body case 1, the actuation unit 2 can be fixed to the main body case 1. The indicator ring 104 is made of transparent plastic material and formed into a ring shape and a light guide portion 107 for introducing an irradiating light of an LED 106 mounted on the circuit board 18 is provided on an upper face side of the indicator ring 104. In this state, the mist opening cover 72 is inserted and mounted into the mist opening 3 and fixed to the nozzle case 11.

The indicator ring 104 and the LED 106 are provided to indicate that the secondary battery 16 is being charged and to indicate a level of remaining power of the secondary battery 16. The LED 106 is formed by three-color LEDs and can indicate that the secondary battery is in a charged state or indicate the remaining power by changing its emitting color or by flashing. As shown in FIG. 6, a connector window 108 for exposing an end portion of the connector 20 is open at a center of the indicator ring 104 and the plug for charging is attached to and detached from the connector 20 through the window 108.

The air pump 14 and the motor 15 in the above-described assembled state face the grip portion 5 with the back wall 1b interposed therebetween. This is for positioning the heavy air pump 14 and motor 15 close to a user's palm when the user places his/her palm on the grip portion 5 and grips the main body case 1 so that the user can hold the main body case 1 without gradually feeling that the sprayer is heavier. Moreover, by holding the main body case 1 without gradually feeling that the sprayer is heavier, the user can lightly spray the mist even when the user sprays while moving the mist device widely around his/her or other person's head, for example. Furthermore, by receiving the user's palm with the grip portion 5 which is recessed inward, it is possible to reliably prevent displacement of the hand in the vertical and peripheral directions.

Figure 2:
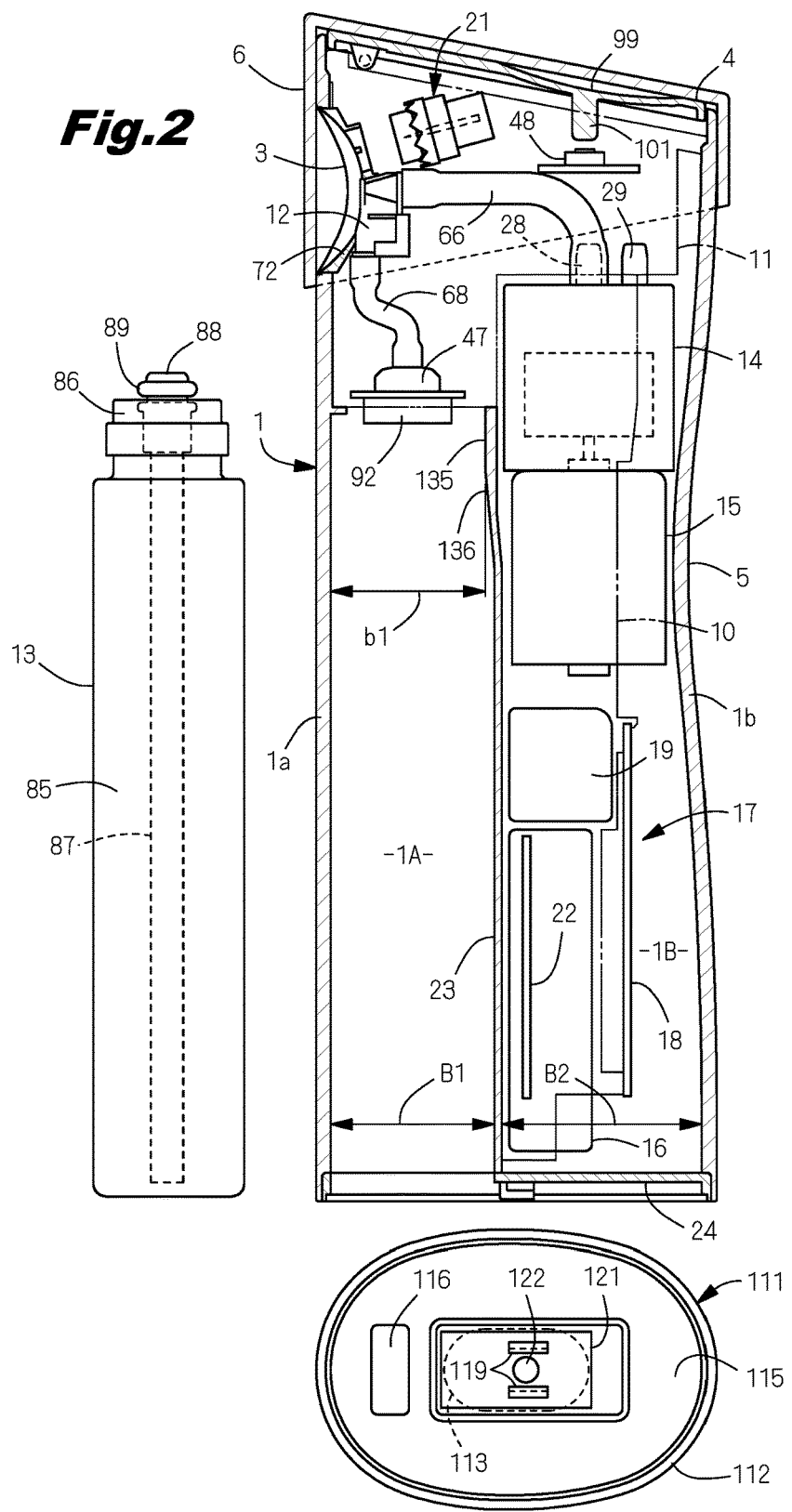

A bottom lid 111 is provided to open and close the bottom opening of the main body case 1 so that the tank 13 can be put into and taken out of the front chamber 1A. As shown in FIGS. 2, 6, and 7, the bottom lid 111 is formed in a shape of an elliptic plate having an endless ring-shaped lid peripheral edge wall 112 and open upward and an operation recessed portion 114 for housing an operating knob 113 is formed on a lower face side of a center of the bottom lid 111 to bulge upward. A bottom wall between the lid peripheral edge wall 112 and a bulging wall of the operation recessed portion 114 functions as a liquid receiving recessed portion 115 for receiving the mist liquid concentrate leaked from the tank 13. The liquid receiving recessed portion 115 is formed in an annular shape along the lid peripheral edge wall 112 and a rubber pressing piece 116 for pressing the tank 13 against the coupling member 47 is fixed to the liquid receiving recessed portion 115 facing a bottom face of the tank main body 85. Because a lower face of the bottom lid 111 surrounding the operation recessed portion 114 is formed to be flat, the mist device in the unused state can be placed and housed by standing the main body case 1.

Between the bottom lid 111 and the inner bottom wall 24, a lock mechanism for locking and retaining the bottom lid 111 mounted to the main body case 1 is provided. The lock mechanism is formed by the operating knob 113 housed in the operation recessed portion 114, paired right and left engagement arms 119 provided integrally with the operating knob 113, paired right and left lid engagement frames 120 provided on a lower face side of the inner bottom wall 24, a slide plate 121 disposed on an upper face of an upper wall of the operation recessed portion 114, and the like. The paired engagement arms 119 protrude above the bottom lid 111 through slide grooves formed in the bottom lid 111. The operating knob 113 and the slide plate 121 are integrated with each other by a pin 122 provided to the operating knob 113 to be able to move together. The engagement arms 119 in a locked state (state shown in FIG. 6) are engaged with the lid engagement frames 120 to prevent the bottom lid 111 from being detached from the main body case 1. If the operating knob 113 is slid backward in FIG. 6, the engagement between the engagement arms 119 and the lid engagement frames 120 is cancelled so that the bottom lid 111 can be detached from the main body case 1.

The lid engagement frames 120 are formed integrally in injection molding of the inner bottom wall 24. At this time, paired right and left removal holes 123 remain after removal of a metal mold above positions where the lid engagement frames 120 are formed (see FIG. 7). In order to prevent entry of liquid droplets and the like from the removal holes 123 into the electrical component section 17, the paired right and left plug-shaped protrusions 124 provided to a lower face of the socket holder 103 close the removal holes 123. By engaging the plug-shaped protrusions 124 in the removal holes 123, backlash of the socket holder 103 in the front-back direction can be prevented and therefore it is possible to appropriately attach and detach the charging plug to and from the connector 20.

FIG. 11 shows a diagrammatic sketch of a circuit configuration of the mist device. If the switch knob 4 is turned on when the mist device is to be used, the motor 15 is driven for rotation via the control circuit mounted on the circuit board 18 and, at the same time, the current regulating circuits forming an ion generating structure are actuated to supply high-voltage current for corona discharge to the central electrode 81 which serves as the discharge electrode. The preceding circuits for the current regulation are formed by an oscillator circuit 127 for converting electric current of the secondary battery 16 into alternating current, a first voltage booster circuit 128 for boosting voltage of the pulse current generated by the oscillator circuit 127, a rectifier circuit 129 for rectifying the pulse current the voltage of which has been boosted to 100 V by the voltage booster circuit 128, and a pulse generating circuit 130 for converting direct current rectified by the rectifier circuit 129 into pulse current again.

The following circuits for the current regulation are formed by a second voltage booster circuit 131 for boosting voltage of the pulse current output from the pulse generating circuit 130 to 4 kV and the diode 132 for setting charge polarity of the mist. As described previously, out of the respective circuits for the current regulation, the circuits from the oscillator circuit 127 to the pulse generating circuit 130 are mounted on the auxiliary circuit board 22 and the voltage booster circuit 131 and the diode 132 are sealed in the resin mold 19.

If the high-voltage current regulated by the respective circuits for the current regulation is supplied between the central electrode 81 and the opposite electrode 82, electrons are emitted from the central electrode 81 due to the corona discharge and bind to oxygen molecules in the air to become the negatively charged or positively charged ion species. The generated ion species are drawn into a high-speed airflow ejected from the nozzle hole 57 and come in contact with the mist ejected together with the airflow to negatively or positively charge the mist. The mist is positively charged when the diode 132 is connected in a forward orientation to the central electrode 81 while the mist is negatively charged when the diode 132 is connected in a backward orientation to the central electrode 81.

The tank 13 is put into and taken out of the front chamber 1A from the bottom opening side of the main body case 1 from which the bottom lid 111 is detached. Therefore, in inserting and mounting the tank 13 into the front chamber 1A, it is difficult to appropriately align a center of the connection portion 86 of the long and narrow tank 13 with a center of the cylindrical wall 92 of the coupling member 47. In order to resolve this inconvenience, a positioning portion 135 and a positioning guide 136 are formed at an upper portion of the division wall 23 as shown in FIG. 4.

To put it concretely, the upper portion of the division wall 23 is brought closer to the front wall 1a of the main body case 1 than the other portion to form the positioning portion 135 integrally with the upper portion of the division wall 23. Furthermore, the positioning guide 136 for receiving a peripheral face of the tank 13 and guiding movement of the tank 13 toward the front wall 1a of the main body case 1 is provided in an inclined state to be continuous from a lower end of the positioning portion 135. The positioning portion 135 and the positioning guide 136 are formed simultaneously with the division wall 23 in molding of the main body case 1. By providing the positioning portion 135 as described above, a front-back width b1 of the front chamber 1A at the upper portion of the division wall 23 from the front wall 1a of the main body case 1 is set to be smaller than a front-back width B1 of a lower portion of the front chamber 1A facing the bottom opening of the main body case 1.

If the positioning portion 135 and the positioning guide 136 are formed at the upper portion of the front chamber 1A as described above, the positioning guide 136 can guide movement of a flat shoulder portion of the tank main body 85 toward the positioning portion 135 immediately before the insertion of the tank 13 into the front chamber 1A is finished. Therefore, by simply inserting the tank 13 into the front chamber 1A, it is possible to align the center of the connection portion 86 with the center of the cylindrical wall 92 of the coupling member 47 to easily couple the tank 13 to the coupling member 47. In coupling the tank 13 to the coupling member 47, the main body case 1 is gripped from a front face side and retained at a tilt with a left hand with the bottom opening positioned at a lower end of the tilted main body case 1 and the tank 13 gripped with a right hand is inserted into the front chamber 1A, for example. At this time, the curved front wall 1a guides a curved wall of the tank 13 having the section similar to the tunnel section while roughly positioning the curved wall and the positioning portion 135 receives the flat shoulder portion of the tank 13 to correct an attitude of the tank 13 in a peripheral direction and therefore it is always possible to appropriately align the center of the connection portion 86 with the center of the cylindrical wall 92. Moreover, because the positioning portion 135 is formed at the upper portion of the front chamber 1A, the large front-back width of the front chamber 1A can be secured on the bottom opening side and, as a result, it is easy to insert the tank 13 into the front chamber 1A.

In FIG. 2, when the front-back width of the front chamber 1A is B1 and the front-back width of the back chamber 1B is B2, the front-back width B2 of the back chamber 1B is set to be larger than the front-back width B1 of the front chamber. This is because diameters (or front-back widths) of the air pump 14 and the motor 15 are larger than a front-back width of the tank 13 and the large-sized air pump 14 and motor 15 need to be housed in the roomy back chamber 1B.

Although the small front-back width B1 of the front chamber results in the small capacity of the tank 13, increase in a vertical dimension of the tank 13 can make up for the reduction in the tank capacity.

To use the mist device, the user places his/her palm on the grip portion 5, pinches and retains right and left walls of the main body case 1 with his/her thumb and a base of the thumb and his/her three fingers, i.e., middle finger, ring finger, and little finger, and presses down the switch knob 4 with his/her index finger to activate the motor 15. The air pump 14 is actuated simultaneously with the activation of the motor 15 to send the pressurized air to the mist nozzle 12 through the air supply tube 66 and the air throttled and increased in the flow velocity by the air passage 61 is blown out of the nozzle hole 57. Therefore, large negative pressure acts on a portion of the liquid passage 63 crossing the air passage 61 and the negative pressure draws up the mist liquid concentrate in the tank 13 through the suction pipe 87, the coupling member 47, and the liquid supply tube 68. Furthermore, the drawn-up mist liquid concentrate is formed into the mist at the upper end of the liquid passage 63 and blown out of the nozzle hole 57 together with the pressurized air. If the mist liquid concentrate is lotion, for example, the mist blown out of the nozzle hole 57 is blown onto the facial skin. Because the switch 48 for activating the motor is the self-return switch, the motor 15 is activated only when the switch knob 4 is being pressed down with the index finger, and the motor 15 is deactivated when the pressing down operation with the index finger is cancelled.

The ion generating structure is activated simultaneously with the activation of the motor 15 to supply the high-voltage (4 kV) pulse current regulated by the respective circuits 127 to 132 to the central electrode 81 via the high-voltage lead. As a result, the corona discharge occurs between the central electrode 81 and the opposite electrode 82, the electrons emitted from the central electrode 81 bind to the oxygen molecules in the air to become the ion species, and the ion species are drawn into the high-speed airflow ejected from the nozzle hole 57 and come in contact with the mist to negatively or positively charge the mist. Because the facial skin (human body) of the user in this state is at the same ground potential as the opposite electrode 82 via a fingertip in contact with the switch knob (contact electrode) 4, lines of electric force are formed from the central electrode 81 toward the facial skin so that the mist charged by the ion species can be attracted toward the skin face.

If the high voltage is applied between the central electrode 81 and the opposite electrode 82 to generate the ion species and the generated ion species are brought in contact with the mist ejected from the mist nozzle 12 as described above, it is possible to appropriately generate the negatively or positively charged mist. Moreover, the potential of the human body can be set to the same potential as the potential of the opposite electrode 82 when the fingertip is in contact with the switch knob 4, the charged mist can be stably attracted to adsorb onto the human body. Incidentally, the human body is normally positively charged and therefore the mist can be attracted to adsorb onto the human body, if the negatively charged mist is generated.

In the state in which the mist device is used as described above, the LED 78 disposed behind the mist nozzle 12 emits the light simultaneously with turning on of the switch knob 4. The light irradiated from the LED 78 is repeatedly reflected and scattered while passing through the transparent mist nozzle 12 and emitted from a peripheral wall of the nozzle hole 57 toward the mist flow. In this way, it is possible to illuminate the mist flow with the scattered soft light to color the mist flow with the emitted color from the LED 78 to thereby create a fantastic atmosphere. The LED 78 serves also as a pilot lamp and lights up and goes out in response to turning on and off of the switch knob 4.

To use the mist device, as described previously, the user places his/her palm on the grip portion 5 and pinches and retains the right and left walls of the main body case 1 with his/her thumb and the base of the thumb and his/her three fingers, i.e., middle finger, ring finger, and little finger. In this retained state, the air pump 14 and the motor 15 which are heavier than the other component parts are positioned close to the user's palm holding and retaining the main body case 1 and the user can firmly grip the mist device while naturally holding and retaining a portion on which a larger amount of weight is concentrated than on the other portion. Therefore, even if the user moves the gripped mist device widely, the user can lightly spray the mist without gradually feeling that the mist device is heavier. Furthermore, because the user's palm is received by the grip portion 5 which is recessed inward, the user can naturally grip the suitable position in a suitable attitude without the necessity of consciously gripping the main body case 1 and it is possible to reliably prevent displacement of the hand in the vertical and peripheral directions when the user moves the mist device widely.

The above-described mist device (sprayer) can be carried out in the following modes.

The sprayer including the mist generating portion and the electrode unit (discharge electrode) 21 and capable of bringing the mist generated by the mist generating portion and the ion species generated by the electrode unit 21 in contact with each other to thereby generate the charged mist, wherein the sprayer has the circuit for applying the voltage to the electrode unit 21 and the contact electrode to be connected to the ground line 134 of the circuit and the contact electrode is provided to the switch operating member 4 of the switch 48 for driving the mist generating portion and the electrode unit 21.

According to the sprayer having the above-described structure, it is possible to properly generate the negatively or positively charged mist. For example, the human body is normally positively charged and therefore the mist can be attracted to adsorb onto the human body, if the negatively charged mist is generated. Moreover, because it is possible to proactively set the potential of the human body to the same potential as the ground potential of the circuit for applying the voltage to the electrode unit 21, the charged mist can be stably attracted to adsorb onto the human body.

The sprayer, wherein the switch 48 for driving the mist generating portion and the electrode unit 21 is formed by the self-return switch, the mist generating portion and the electrode unit 21 can be driven continuously in a state in which the switch operating member 4 is switched into an ON state, and actuation of the mist generating portion and the electrode unit 21 is stopped when the fingertip separates from the switch operating member 4 and the switch operating member 4 is switched into an OFF state.

As described above, because the user necessarily switches the switch 48 while in contact with the switch operating member 4 serving also as the contact electrode to use the sprayer, the user can unconsciously perform the function of attracting the charged mist to his/her body.

The sprayer, wherein the mist generating portion is formed by the mist nozzle 12, the mist nozzle 12 includes the air passage 61 for guiding the flow of the pressurized air, the liquid passage 63 for guiding the flow of the mist liquid concentrate, and the nozzle hole 57, and the mist liquid concentrate can be drawn up by the action of the negative pressure acting on the portion of the liquid passage 63 crossing the air passage 61, formed into the mist, and ejected from the nozzle hole 57 together with the airflow.

FIG. 13 shows an embodiment formed by changing a part of the air pump 14. Here, an intake portion 29 is provided on a front side of an upper portion of an air pump 14 and a discharge portion 28 is provided behind the intake portion 29. Moreover, the intake portion 29 is formed in a shape of an inverted L and an intake port 33 of the intake portion 29 protrudes from an outer face of a back wall 1*b* of a nozzle case 11 so as to be open behind a discharge portion 28. In this case, by forming an opening in a position of an upper wall of the nozzle case 11 around a seal rubber 100, air which has entered an inner face side of a switch knob 4 through a clearance between the switch knob 4 and a main body case 1 can be taken in from the intake port 33. The intake port 33 can be open in an arbitrary orientation as long as the intake port 33 is positioned behind the discharge portion 28. For example, the intake port 33 of the intake portion 29 formed in the inverted L shape can be open forward or sideways. In these cases, it is essential only that an opening position of the intake port 33 be positioned behind the discharge portion 28.

Although the intake portion 29 is formed in the inverted L shape in the above-described embodiment, it is not an essential. For example, an elastically deformable intake tube for drawing in of air may be connected to an intake portion 29 in a state shown in FIG. 3 and led out with its open end (intake port 33) facing a space on an inner face side of a switch knob 4. If the intake port 33 is disposed in the space on the inner face side of the switch knob 4 in this manner, it is possible to prevent development of negative pressure in a nozzle case 11 by intake action of an air pump 14 and therefore a mist nozzle 12 can effectively generate mist. Moreover, because the open end of the intake tube is covered with the switch knob 4, addition of the intake tube does not impair an impression of an external appearance of a mist device. Moreover, a joint portion similar to the intake portion 29 may be provided to a lower face side of an upper wall of a nozzle case 11 and the joint portion and the intake portion 29 may be connected by an elastically deformable intake tube so as to draw in air from a space on an inner face side of the switch knob 4.

FIG. 14 shows still another embodiment of the air pump 14. Here, pressurized air is supplied by an electromagnetic pump in which diaphragm pumps (air pumps) 14 are respectively disposed above and below a linear motor (motor) 15. The linear motor 15 is formed by disposing an E-shaped core 141 and a back core 142 so that both the cores 141, 142 face each other and an oscillator 143 is disposed between both the cores 141 and 142 in a housing 140. A coil is wound around only the E-shaped core 141 out of both the cores 141, 142. Permanent magnets are mounted to the oscillator 143 and the oscillator 143 is reciprocated by attraction or repulsion between both the cores 141, 142 and the permanent magnets to vertically operate the diaphragms 144 provided to upper and lower opposite ends of the oscillator 143 to thereby pressurize air drawn in from an intake portion 29 and send the air from a discharge portion 28. A reference sign 145 denotes an intake valve and a reference sign 146 denotes an exhaust valve.

FIG. 15 shows still another embodiment of the sprayer. Here, an air pump 14 and a motor 15 are disposed in an upper portion of a back chamber 1B to be adjacent to each other in a front-back direction and an electrical component section 17 including a battery 16 is housed in a lower portion of the back chamber 1B. An intake tube 148 is connected to an intake portion 29, the entire intake tube 148 is bent into a J shape, and an intake port 33 of the intake tube 148 is positioned below the motor 15. In this manner, it is essential only that the air pump 14 and the motor 15 be provided on a back half side in a main body case 1. Moreover, placement of devices such as the (secondary) battery 16, a circuit board 18, and a resin mold 19 in the electrical component section 17 can be changed as necessary.

Although the sectional shape of the main body case 1 is the ellipse which is long in the front-back direction, it is not an essential. For example, the sectional shape may be an oval or an egg shape which is long in the front-back direction. The main body case 1 may be formed into a vertically long cylindrical shape by joining two parts divided in the front-back, right-left, or vertical direction. Although the entire switch operating member 4 covering the upper opening plane of the main body case 1 swings up and down about the pin 98 in the above-described embodiment, it is not an essential. A switch operating member 4 may be provided to a part of a wall face covering an upper opening plane of a main body case 1 to switch a switch 48. The switch operating member 4 in this case may be formed in a push button shape or a slide knob shape. Moreover, although the positioning portion 135 and the positioning guide 136 are formed on the division wall 23, it is not an essential. It is essential only that a positioning portion 135 and a positioning guide 136 be formed on an inner peripheral face of an upper portion of a front chamber 1A. For example, a plurality of rib-shaped protrusions may be formed on inner faces of a front wall 1*a* and right and left walls of a main body case 1 to respectively function as the positioning portion 135 and the positioning guide 136.

A bottom lid 111 may be detachably press-fitted with and mounted to an inner bottom wall 24 or a main body case 1. Furthermore, the lock mechanism of the bottom lid 111 does not necessarily has to be the structure described in the embodiment. An operating knob 113 may be turned to engage and disengage engagement arms 119 with and from lid engagement frames 120. At least one engagement arm 119 may be provided.

An air supply tube 66 and a liquid supply tube 68 may be formed by hard-plastic tube members or metal tubes if necessary. In this case, the tube members in shapes of straight tubes may be bent to form the air supply tube 66 and the liquid supply tube 68. The division wall 23 does not have to be formed as the vertical wall and may be formed in a forward or backward tilted state. A tube support wall 44 may be formed in a gutter shape. As a fastening member 102, a screw, a bolt, or a nut may be employed. The sprayer according to the present invention may be for personal or professional use and may be used as an inhaler for spray-dispensing mist of medicinal solution into a throat and a mouth cavity.

DESCRIPTION OF REFERENCE SIGNS

1 Main body case
2 Actuation unit
3 Mist opening
4 Switch operating member (switch knob)
10 Electrical component case 11 Nozzle case
12 Mist nozzle
13 Tank
14 Air pump
15 Motor
16 Battery (secondary battery)
21 Electrode unit
28 Discharge portion
35 Partition wall
43 Retaining hole
44 Tube support wall
47 Coupling member
57 Nozzle hole
60 Air supply opening
66 Air supply tube
68 Liquid supply tube

The invention claimed is:

1. A sprayer comprising:
a mist nozzle; a tank for storing a mist liquid concentrate; an air pump; a motor and a battery for driving the pump; and a main body case for housing these respective devices,
wherein the mist nozzle is supported by a nozzle case fixed in the main body case, and
an air supply opening of the mist nozzle and a discharge portion of the air pump are connected via an air supply tube,
wherein the nozzle case is formed by a left case body and a right case body which are two parts divided in a left-right direction, the mist nozzle is pinched and fixed by the left and right case bodies, and the left and right case bodies pinch a plurality of positions of an upper portion of an electrical component case to thereby integrate the electrical component case and the nozzle case into an actuation unit,
a middle portion of the air supply tube is pinched and fixed by a retaining hole provided in a junction between the left case body and the right case body so as not to move freely, and
wherein the actuation unit is detachably inserted and mounted into the main body case.

2. The sprayer according to claim 1,
wherein the nozzle case is mounted to an upper portion in the main body case, a switch operating member for switching a switch for the motor is disposed above the main body case, and
an upper wall of the nozzle case serves also as a switch base for supporting the switch operating member.

3. The sprayer according to claim 2,
wherein a seal body for sealing a switch window, which is open in the upper wall of the nozzle case, in a watertight manner is mounted to an opening edge of the switch window and
a switching operation by the switch operating member is transmitted to the switch via the seal body.

4. The sprayer according to claim 1,
wherein a coupling member, to which a connection portion provided to an upper portion of the tank is to be connected, is fixed to a lower end of the nozzle case,
the mist nozzle and the coupling member are connected via a liquid supply tube, and
bent passage portions are formed at two positions of a middle portion of the liquid supply tube so that a center of a connection between the mist nozzle and the liquid supply tube is positioned forward of a center of a connection between the coupling member and the liquid supply tube.

5. The sprayer according to claim 1,
wherein partition walls crossing the air supply tube are provided to the left case body and the right case body,
the retaining hole and a tube support wall for supporting the middle portion of the air supply tube are formed at a junction of the partition walls, and
the tube support wall guides the middle portion of the air supply tube in a curved manner to retain a bent portion of the air supply tube in a predetermined shape.

6. A sprayer comprising:
a mist nozzle; a tank for storing a mist liquid concentrate; an air pump; a motor and a battery for driving the pump; and a main body case for housing these respective devices,
wherein the mist nozzle is supported by a nozzle case fixed in the main body case,
wherein an air supply opening of the mist nozzle and a discharge portion of the air pump are connected via an air supply tube,
wherein an electrical component case is disposed below a back portion of the nozzle case,
wherein the air pump and the motor are mounted in an upper portion of the electrical component case,
wherein the air pump, the motor, the battery, and a circuit board are mounted in the electrical component case,
a fastening member fastens a left case body and a right case body of the nozzle case while both the case bodies pinch a plurality of positions of the upper portion of the electrical component case to thereby integrate the electrical component case and the nozzle case into an actuation unit, and
the actuation unit is detachably inserted and mounted into the main body case.

7. A sprayer comprising:
an air pump; a motor and a battery for driving the pump; a mist nozzle; a tank for storing a mist liquid concentrate; and a cylindrical main body case for housing these respective devices,
wherein a mist opening is open in an upper portion of a front wall of the main body case, the mist nozzle is disposed on an inner side of the mist opening,
the air pump for supplying pressurized air to the mist nozzle, the motor for driving the pump, and an electrical component section including the battery are disposed on a back half side in the main body case, and
the tank extending from a bottom portion of the main body case to a position below the mist nozzle is detachably housed on a front half side in the main body case;
wherein an inside of the main body case is divided into a front chamber on a front side and a back chamber on a back side by a division wall continuous in the vertical direction, the tank is housed in the front chamber, and the air pump, the motor, and the electrical component section including the battery are housed in the back chamber; and
wherein a coupling member, to which a connection portion provided to an upper portion of the tank is to be connected, is fixed to an upper end of the front chamber, and
a positioning portion, configured to receive a peripheral face of the tank and position the connection portion with respect to the coupling member, is formed on an inner face of an upper portion of the front chamber,
wherein an upper portion of the division wall is brought closer to the front wall of the main body case than the other portion of the division wall so as to form the positioning portion integrally with the division wall.

8. The sprayer according to claim 7,
wherein the mist nozzle and the tank are disposed on the front half side in the main body case, and the air pump, the motor, and the electrical component section are disposed on the back half side in the main body case, and the tank is formed to be vertically long so that an upper end of the tank reaches a middle portion in a vertical direction of the air pump.

9. The sprayer according to claim 8,
wherein the air pump, the motor, and the electrical component section are disposed, in order from above, on the back half side in the main body case.

10. The sprayer according to claim 7,
wherein a front-back width in the back chamber is larger than a front-back width in the front chamber.

11. The sprayer according to claim 7
wherein a bottom lid for opening and closing a bottom opening of the main body case is provided to a lower end of the main body case, the bottom lid is formed in a plate shape including an endless ring-shaped lid peripheral edge wall and open upward, and a liquid receiving recessed portion for receiving the mist liquid concentrate leaked from the tank is formed in an annular shape on an inner face of the bottom lid.

12. The sprayer according to claim 11,
wherein an inner bottom wall for closing a lower opening of the back chamber is fixed to the lower end of the main body case, a socket holder for supporting a connector is fixed to an upper face of the inner bottom wall, a lock mechanism for locking and retaining the bottom lid mounted to the main body case is provided between the bottom lid and the inner bottom wall, the lock mechanism includes an operating knob disposed on a lower face side of the bottom lid, an engagement arm provided to the operating knob and protruding above the bottom lid, and a lid engagement frame provided to a lower face side of the inner bottom wall, and a plug-shaped protrusion provided to a lower face of the socket holder is engaged in a removal hole, open in the inner bottom wall to correspond to a position where the lid engagement frame is formed, so that the plug-shaped protrusion closes the removal hole.

13. The sprayer according to claim 7,
wherein the main body case is formed to have an elliptic section having a long axis in a front-back direction, a switch operating member for switching a switch for activating the motor is disposed at an upper end of the main body case, a grip portion for receiving a user's palm is formed in a recessed manner near an upper portion of a back face of the main body case, and the air pump and the motor are disposed in the back chamber facing the grip portion.

14. The sprayer according to claim 7,
wherein an air supply opening of the mist nozzle and a discharge portion of the air pump are connected via an air supply tube, and a liquid supply opening of the mist nozzle and an outlet portion of the coupling member are connected via a liquid supply tube, and an intake port of an intake portion of the air pump is positioned behind the discharge portion.

* * * * *